United States Patent
Slukvin et al.

(10) Patent No.: US 12,098,390 B2
(45) Date of Patent: *Sep. 24, 2024

(54) GENERATING VASCULOGENIC CELL POPULATIONS

(71) Applicant: WISCONSIN ALUMNI RESEARCH FOUNDATION, Madison, WI (US)

(72) Inventors: Igor Slukvin, Verona, WI (US); Akhilesh Kumar, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/403,202

(22) Filed: Aug. 16, 2021

(65) Prior Publication Data
US 2021/0380947 A1 Dec. 9, 2021

Related U.S. Application Data

(60) Continuation of application No. 15/835,850, filed on Dec. 8, 2017, now Pat. No. 11,091,738, which is a division of application No. 14/303,428, filed on Jun. 12, 2014, now Pat. No. 9,868,939.

(60) Provisional application No. 61/834,218, filed on Jun. 12, 2013.

(51) Int. Cl.
| | |
|---|---|
| *C12N 5/077* | (2010.01) |
| *A61K 35/34* | (2015.01) |
| *A61K 35/44* | (2015.01) |
| *A61K 35/28* | (2015.01) |

(52) U.S. Cl.
CPC ............ *C12N 5/0661* (2013.01); *A61K 35/34* (2013.01); *A61K 35/44* (2013.01); *A61K 35/28* (2013.01); *C12N 2500/90* (2013.01); *C12N 2501/11* (2013.01); *C12N 2501/115* (2013.01); *C12N 2501/135* (2013.01); *C12N 2501/15* (2013.01); *C12N 2501/165* (2013.01); *C12N 2501/999* (2013.01); *C12N 2506/02* (2013.01); *C12N 2506/1346* (2013.01); *C12N 2506/45* (2013.01)

(58) Field of Classification Search
CPC ....... C12N 5/0661; A61K 35/34; A61K 35/44
See application file for complete search history.

(56) References Cited

U.S. PATENT DOCUMENTS

| | | |
|---|---|---|
| 6,143,292 A | 11/2000 | Slavin |
| 6,326,198 B1 | 12/2001 | Emerson et al. |
| 6,383,481 B1 | 5/2002 | Ikehara et al. |
| 6,447,765 B1 | 9/2002 | Horwitz |
| 9,868,939 B2 | 1/2018 | Slukvin et al. |
| 9,938,499 B2 | 4/2018 | Slukvin et al. |
| 11,091,738 B2 | 8/2021 | Slukvin et al. |
| 2011/0236971 A2 | 9/2011 | Vodyanyk et al. |
| 2012/0148546 A1 | 6/2012 | Ayelet |
| 2014/0004046 A1 | 1/2014 | Raghunath |
| 2014/0273211 A1 | 9/2014 | Slukvin |

OTHER PUBLICATIONS

Xia et al. "In vitro-and in vivo-induced transgene expression in human embryonic stem cells and derivatives." Stem Cells 26(2): 525-533 (2008).
Xiong. "Characterization of mesenchymal stem/progenitor cells and their progeny from non-fetal tissue sources," http://files.webb.uu.se/uploader/858/1509-Anqi-Xiong-uppsats.pdf pp. 1-25, 2010.
Yu et al. "Induced pluripotent stem cell lines derived from human somatic cells." Science 318(5858):1917-1920 (2007).
Amit et al. "Suspension culture of undifferentiated human embryonic and induced pluripotent stem cells." Stem Cell Reviews & Reports 6(2):248-259 (2010).
Armulik et al. "Endolhelial/pericyte interactions." Circulalion research 97(6): 512-523 (2005).
Armulik et al "Pericytes: developmental physiological and pathological perspectives problems and promises." Developmental Cell 21(2):193-215 (2011).
Asahina et al. "Septum transversum-derived mesothelium gives rise to hepatic slellale cells and perivascular mesenchymal cells in developing mouse liver." Hepalology 53(3): 983-995 (2011).
Bergers et al. "The role of pericytes in blood-vessel formation and maintenance." Neuro-oncology 7(4): 452-464 (2005).
Cai et al.. "A myocardial lineage derives from Tbx18 epicardial cells." Nature 454(7200): 104-108 (2008).
Chambers et al. "Global expression profiling of fibroblast responses to transforming growth factor-β 1 reveals the induction of inhibitor of differentiation-1 and provides evidence of smooth muscle cell phenotypic switching." Am J Pathol 162(2):533-546 (2003).
Cheung et al. "Generation of human vascular smooth muscle subtypes provides insight into embryological origin-dependent disease susceptibility." Nature Biotechnology 30(2):165-173 (2012).
Crisan et al. "A perivascular origin for mesenchymal stem cells in multiple human organs." Cell Stem Cells 3(3):301-313 (2008).
Crisan et al.,"Perivascular multipotent progenitor cells in human organs." Annals of the New York Academy of Sciences 1176(1):118-123 (2009).
Dallot et al. "Contraction of cultured human uterine smooth muscle cells after stimulation with endothelin-1." Biol Reprod 68(3):937-942 (2003).
Dar et al. "Multipotent vasculogenic pericytes from human pluripotent stem cells promote recovery of murine schemic limb." Circulation 125(1): 87-99 (2012).

(Continued)

*Primary Examiner* — Laura Schuberg
(74) *Attorney, Agent, or Firm* — McDonnell Boehnen & Berghoff, LLP

(57) ABSTRACT

The present invention relates generally to methods and compositions useful for therapeutic vascular tissue engineering. In particular, the present invention provides methods for generating substantially pure populations of vasculogenic cells from human mesenchymal progenitors, and methods and compositions for clinical applications in the field of regenerative medicine.

8 Claims, 11 Drawing Sheets
(11 of 11 Drawing Sheet(s) Filed in Color)
Specification includes a Sequence Listing.

(56) References Cited

OTHER PUBLICATIONS

De Lange et al. "Lineage and morphogenetic analysis of the cardiac valves." Circulation research 95(6): 645-654 (2004).
Flamme et al. "Vascular endothelial growth factor (VEGF) and VEGF receptor (flk-1) are expressed during vasculogenesis and vascular differentiation in the quail embryo." Developmental biology 169(2): 699-712 (1995).
Harris et al. "Differentiation of adult stem cells into smooth muscle for vascular tissue engineering." The Journal of Surgical Research 168(2): 306-14 (2011).
Inman et al. "SB-431542 is a potent and specific inhibitor of transforming growth factor-I! superfamily type I activin receptor-like kinase (ALK) receptors ALK4, ALK5, and ALK7." Mol. Pharmacol. 62(1):65-74 (2002).
Jiang et al. "Fate of the mammalian cardiac neural crest." Development 127(8):1607-1616 (2000).
Kim et al. "Human peripheral blood-derived CD31 + cells have robust angiogenic and vasculogenic properties and are effective for treating ischemic vascular disease." J. Am. Coll. Cardiol. 56(7):593-607 (2010).
Kinoshita et al. "Identification of human endomucin-1 and -2 as membrane-bound O-sialoglycoproteins with anti-adhesive activity." FEBS Lett. 499(1-2):121-126 (Jun. 2001).
Kubota et al. "Isolation and function of mouse tissue resident vascular precursors marked by myelin protein zero." The Journal of Experimental Medicine 208(5):949-960 (2011).
Langmead et al. "Ultrafast and memory-efficient alignment of short DNA sequences to the human genome." Genome Biology 10(3):R25 (2009).
Le Lievre et al. "Mesenchymal derivatives of the neural crest: analysis of chimaeric quail and chick embryos." Journal of embryology and experimental morphology 34(1): 125-154 (1975).
Lee et al. "Revisiting cardiovascular regeneration with bone marrow-derived angiogenic and vasculogenic cells." British journal of pharmacology 169(2): 290-303 (2013).
Leeven et al. "Mice deficient for PDGF B show renal cardiovascular and hematological abnormalities." Genes & Development 8:1875-87 (1994).
Levenberg et al. "Endothelial cells derived from human embryonic stem cells." Proceedings of the National Academy of Sciences 99(7): 4391-4396 (2002).
Li et al. "RNA-Seq gene expression estimation with read mapping uncertainty." Bioinformatics 26(4):493-500 (2010).
Li et al. "RSEM: accurate transcript quantification from RNA-Seq data with or without a reference genome." BMC bioinformatics 12(1):323 (2011).
Maeda et al. "Tbx1 is regulated by forkhead proteins in the secondary heart field." Developmental dynamics 235(3): 701-710 (2006).
Majesky "Developmental basis of vascular smooth muscle diversity." Arteriosclerosis thrombosis and vascular biology 27(6):1248-1258 2007.
Majesky et al. "Vascular Smooth Muscle Progenitor Cells Building and Repairing Blood Vessels." Circulation Research 108(3): 365-377 (2011).
Moonen et al. "Endothelial progenitor cells give rise to pro-angiogenic smooth muscle-like progeny." Cardiovascular research 86(3): 506-515 (2010).
Nakamura et al. "Neural crest cells retain multipotential characleristics in the developing valves and label the cardiac conduction system." Circulation research 98(12):1547-1554 (2006).
Noden "The control of avian cephalic neural crest cytodifferentialion: I. Skeletal and connective tissues." Developmental biology 67(2): 296-312 (1978).
Okamoto et al. "EDG3 is a functional receptor specific for sphingosine 1-phosphale and 32 sphingosylphosphorylcholine with signaling characteristics distinct from EDG1 and AGR16." Biochemical and biophysical research communications 260(1): 203-208 (1999).
Park et al. "Efficient and simultaneous generation of hemalopoietic and vascular progenitors from human induced pluripotenl stem cells." Cytometry Part A 83(1):114-126 (2013).
Pfaffl "A new mathematical model for relative quantification in real-lime RT-PCR." Nucleic acids research 29(9): e45-e45 (2001).
Pouget et al. "Sclerotomal origin of vascular smooth muscle cells and pericytes in the embryo." Developmental biology 315(2): 437-447 (2008).
Que et al. "Mesothelium contributes to vascular smooth muscle and mesenchyme during lung development." Proceedings of the National Academy of Sciences 105(43):16626-16630 (2008).
Reyes et al. "Purification and Ex Vivo Expansion of Postnatal Human Marrow Mesodermal Progenitor Cells" Blood, vol. 98, American Society of Hematology; 13 pages, Nov. 1, 2001.
Risau et al. "Vasculogenesis." Annual review of cell and developmental biology 11(1):73-91 (1995).
Rossant et al. "Signaling pathways in vascular development." Annual review of cell and developmental biology 18(1):541-573 (2002).
Ross et al. "Cytokine-induced differentiation of multipotent adult progenitor cells into functional smooth muscle cells." The Journal of Clinical Investigation 116(12):3139-3149 (2006).
Slukvin et al. "Endothelial origin of mesenchymal stem cells." Cell Cycle 10(9):1370-1373 (2011).
Soriano et al. "Abnormal kidney development and hematological disorders in PDGF beta-receptor mutant mice." Genes & development 8(16):1888-1896 (1994).
Thomson et al. "Embryonic stem cell lines derived from human blastocysts." science 282(5391):1145-1147 (1998).
Vodyanik et al. "Human embryonic stem cell-derived CD34+ cells: efficient production in the coculture with OP9 stromal cells and analysis of lymphohemalopoielic potential." Blood 105(2):617-626 (2005).
Vodyanik et al. "Hemaloendolhelial differentiation of human embryonic stem cells." Currenl Protocols in Cell Biology, Chapter 23 Unit 23.6 (2007).
Vodyanik et al. "A mesoderm-derived precursor for mesenchymal stem and endothelial cells." Cell Stem Cell 7(6): 718-729 (2010).
Waldo et al. "Conolruncal myocardium arises from a secondary heart field." Development 128(16):3179-3188 (2001).
Wilm et al. "The serosal mesothelium is a major source of smooth muscle cells of the gut vasculature." Development 132(23):5317-5328 (2005).

B.

C.

FIGS. 4A-4D
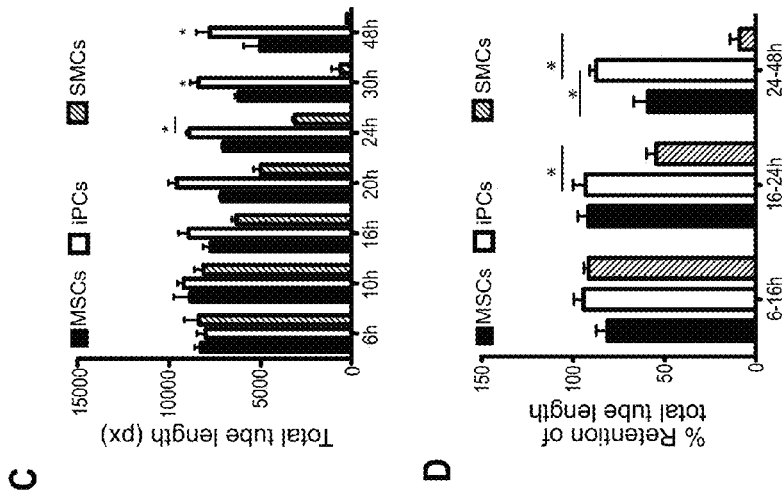
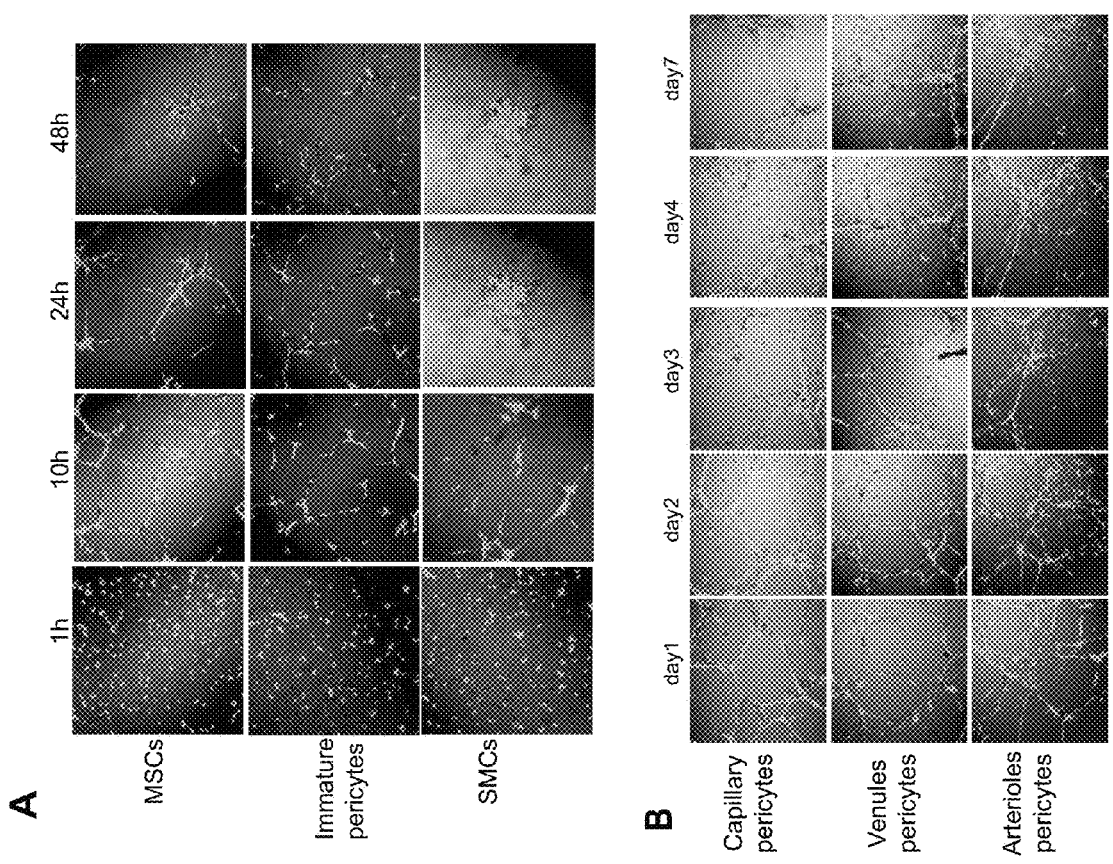

GENERATING VASCULOGENIC CELL POPULATIONS

CROSS-REFERENCE TO RELATED APPLICATIONS

This application is a continuation of U.S. patent application Ser. No. 15/835,850, filed Dec. 8, 2017, which is a divisional of U.S. patent application Ser. No. 14/303,428, filed Jun. 12, 2014, now U.S. Pat. No. 9,868,939, issued Jan. 16, 2018, which claims the benefit of U.S. Provisional Patent Application No. 61/834,218, filed Jun. 12, 2013, both of which are incorporated herein by reference in their entireties.

STATEMENT REGARDING FEDERALLY SPONSORED RESEARCH

This invention was made with government support under GM081629 and HL099773 awarded by the National Institutes of Health. The government has certain rights in the invention.

REFERENCE TO A SEQUENCE LISTING SUBMITTED VIA EFS-WEB

This application includes an electronically submitted Sequence Listing in .txt format. The .txt file contains a sequence listing entitled "2021-08-16_960296-04164 Sequence Listing P13036US04.txt" and was created on Aug. 10, 2021, and is 3,972 bytes in size. The Sequence Listing contained in this .txt file is part of the specification and is hereby incorporated herein in its entirety.

FIELD OF THE INVENTION

The present invention relates generally to methods for obtaining cells for therapeutic vascular tissue engineering. In particular, the invention described herein relates to methods for generating substantially pure populations of vasculogenic cells derived from a colony of mesenchymal progenitors such as a MAB-derived colony of mesenchymal progenitors.

BACKGROUND

Human pluripotent stem cells (human embryonic stem cells and induced pluripotent stem cells (collectively hPSCs)) have the potential to differentiate into any cell type of the human body. These cells provide access to the earliest stages of human development and offer a plentiful platform for the derivation of large number of specialized cell types useful for tissue engineering and therapeutic purposes. To date, our ability to harness the differentiation potential of human pluripotent stem cells has been hampered by incomplete understanding of the factors that govern their differentiation and direct the cells down lineages derived from the three germ layers. Accordingly, there remains a need in the art for methods and compositions for guiding pluripotent cell differentiation in vitro and for developing scalable sources of differentiated and precursor cells suitable for therapeutic tissue engineering protocols.

BRIEF SUMMARY OF THE INVENTION

In a first aspect, the present invention provides a method for generating an isolated population of primate vasculogenic cells. The method comprises contacting a colony of primate mesenchymal progenitors to a serum-free culture medium comprising an amount of at least one factor selected from sphingosylphosphorylcholine (SPC) and Transforming Growth Factor Beta (TGFβ) that is effective to promote differentiation of the contacted mesenchymal progenitors to vasculogenic cells; culturing the contacted mesenchymal progenitors on a coated plate under conditions that promote differentiation of the mesenchymal progenitors to vasculogenic cells; and isolating the vasculogenic cells.

The mesenchymal progenitors can be PDGFRβ$^+$ (Platelet Derived Growth Factor Receptor β)/EMCN$^{high}$/CD105$^{low}$48$^-$/CD73$^-$/CD31$^-$. The colony of primate mesenchymal progenitors can be derived from a primate mesenchymoangioblast (MAB). The primate can be human. The isolated vasculogenic cells can be smooth muscle cells. The isolated vasculogenic cells can express at least one molecular marker of smooth muscle cells. The at least one molecular marker of smooth muscle cells is selected from α-SMA (alpha-smooth muscle actin), calponin, desmin, SM22 (Smooth muscle protein of 22 kDa), MYOCD (myocardin), and MYH11 (Myosin Heavy Chain 11). The colony of mesenchymal progenitors colony can be clonal. The colony of mesenchymal progenitors can be polyclonal. The coated plate can be fibronectin-coated, gelatin-coated, or collagen-coated. An effective amount of SPC is between about 2 μM and about 5 μM. An effective amount of TGFβ is between about 1 ng/mL and about 4 ng/mL.

In another aspect, the present invention provides a method for generating an isolated population of primate vasculogenic cells. The method comprises culturing a colony of primate mesenchymal progenitors to a serum-free culture medium comprising Platelet-Derived Growth Factor BB (PDGF-BB) in an amount effective to promote differentiation of the mesenchymal progenitors to vasculogenic cells; culturing the contacted mesenchymal progenitors on a coated plate under conditions that promote differentiation of the mesenchymal progenitors to vasculogenic cells; and isolating the vasculogenic cells.

The mesenchymal progenitors can be PDGFRβ$^+$ (Platelet Derived Growth Factor Receptor β)/EMCN$^{high}$/CD105$^{low}$/CD248$^-$/CD73$^-$/CD31$^-$. The colony of primate mesenchymal progenitors can be derived from a primate mesenchymoangioblast (MAB). The primate can be human. The isolated vasculogenic cells can be immature pericytes. The immature pericytes can express RGS5 (Regulator of G-protein Signaling 5), PDGFRβ, ANG-1 (angiopoietin-1), CD146, CD44, CD90, CD13, and NG2 (Nerve/Glial antigen 2). The immature pericytes do not express or have low expression relative to a smooth muscle cell of at least one molecular marker of smooth muscle cells selected from α-SMA, calponin, desmin, SM22, MYOCD, and MYH11.

In some cases, the method further comprises culturing the immature pericytes in the presence of a maturation culture medium comprises a TGFβ receptor inhibitor and PDGF-BB under conditions that promote maturation of immature pericytes to mature pericytes. The TGFβ receptor inhibitor can be SB-431542. The mature pericyte can be a NG2$^{high}$/α-SMA$^{low}$/RGS5$^+$ capillary pericyte. The maturation culture medium can further comprise PDGF-BB and Vascular Endothelial Growth Factor-A (VEGF) and the mature pericyte is a NG2$^{low}$/α-SMA$^{high}$/RGS5$^+$ venule pericyte. The maturation culture medium can further comprise PDGF-BB, VEGF, and Epidermal Growth Factor 2 (EGF2), and the mature pericyte is a NG2$^{high}$/α-SMA$^{high}$/RGS5$^+$ arteriole pericyte. The colony of mesenchymal progenitors can be clonal. The colony of mesenchymal progenitors can be polyclonal. The coated plate can be fibronectin-coated, gelatin-coated, or collagen-coated.

In another aspect, the present invention provides an isolated population of human immature pericytes obtained according to a method of the invention. At least 90% of cells within the population can be human immature pericytes and PDGFRβ$^+$, NG2$^+$, CD146$^+$, CD73$^+$, and CD44$^+$. At least 95% of cells within the population can be human immature pericytes and PDGFRβ$^+$, NG2$^+$, CD146$^+$, CD73$^+$, and CD44$^+$.

In a further aspect, the present invention provides an isolated population of human capillary pericytes obtained according to a method of the invention. At least 90% of cells within the population can be human capillary pericytes and NG2$^{high}$/α-SMA$^{low}$/RGS5$^+$.

In another aspect, the present invention provides an isolated population of human venule pericytes obtained according to a method of the invention. At least 90% of cells within the population can be human venule pericytes and NG2$^{low}$/α-SMA$^{high}$/RGS5$^+$.

In another aspect, the present invention provides an isolated population of human arteriole pericytes obtained according to a method of the invention. At least 90% of cells within the population can be human arteriole pericytes and NG2$^{high}$/α-SMC$^{high}$/RGS5$^+$.

In yet another aspect, the present invention provides an isolated population of vasculogenic cells obtained by a method of the invention. At least 90% of cells within the population can be human smooth muscle cells and α-SMA$^+$, calponin$^+$, desmin$^+$, MYOCD$^+$, and MYH11$^+$. In some cases, at least 95% of cells within the population are human smooth muscle cells and are α-SMA$^+$, calponin$^+$, desmin$^+$, MYOCD$^+$, and MYH11$^+$.

The present invention also provides a method for transplantation in a subject in need thereof. The method comprises providing to the subject the population of cells described herein. Also provided by the present invention is a method for treating a disorder requiring cell or tissue replacement in a subject in need thereof. The method comprises providing to the subject a therapeutically effective amount of a population of cells, whereby the provided cells treat the disorder requiring cell or tissue replacement in the subject.

In another aspect, the present invention provides a pharmaceutical composition comprising vasculogenic cells obtained by contacting a colony of primate mesenchymal progenitors to a serum-free culture medium comprising at least one factor selected from SPC and TGFβ in an amount effective to promote differentiation of the contacted mesenchymal colony to vasculogenic cells.

In yet another aspect, the present invention provides a pharmaceutical composition comprising vasculogenic cells obtained by contacting a colony of primate mesenchymal progenitors to a serum-free culture medium comprising PDGF-BB in an amount effective to promote differentiation of the contacted mesenchymal progenitors to vasculogenic cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4D provide images and data demonstrating stabilization of vascular tubes by MSCs, iPCs, and SMCs. (A) Images of H9-hESC-EGFP derived MSCs, immature pericytes, and SMCs co-cultured (2:1) with HUVECsin pre-solidified Matrigel® in EGM™-2 Endothelial Cell Growth Medium-2 ("EGM2"). The cells were incubated for different time points and photographed using Nikon Eclipse Ti-E configured with an MR confocal system and motorized stage (Nikon Instruments Inc. Melville, NY). (B) Images of mature pericytes (capillary, venule, and arteriole pericytes). (C) Quantification of total tube length and (D) retention of total tube length was quantified by using the Wimasis image analysis software (Wimasis GmbH, Munich, Germany) for MSCs, iPCs, and SMCs. Results are displayed as mean±SE (*p<0.01). Results are representative of three independent studies.

DETAILED DESCRIPTION OF THE INVENTION

Figures 1A, 1B, 1C:
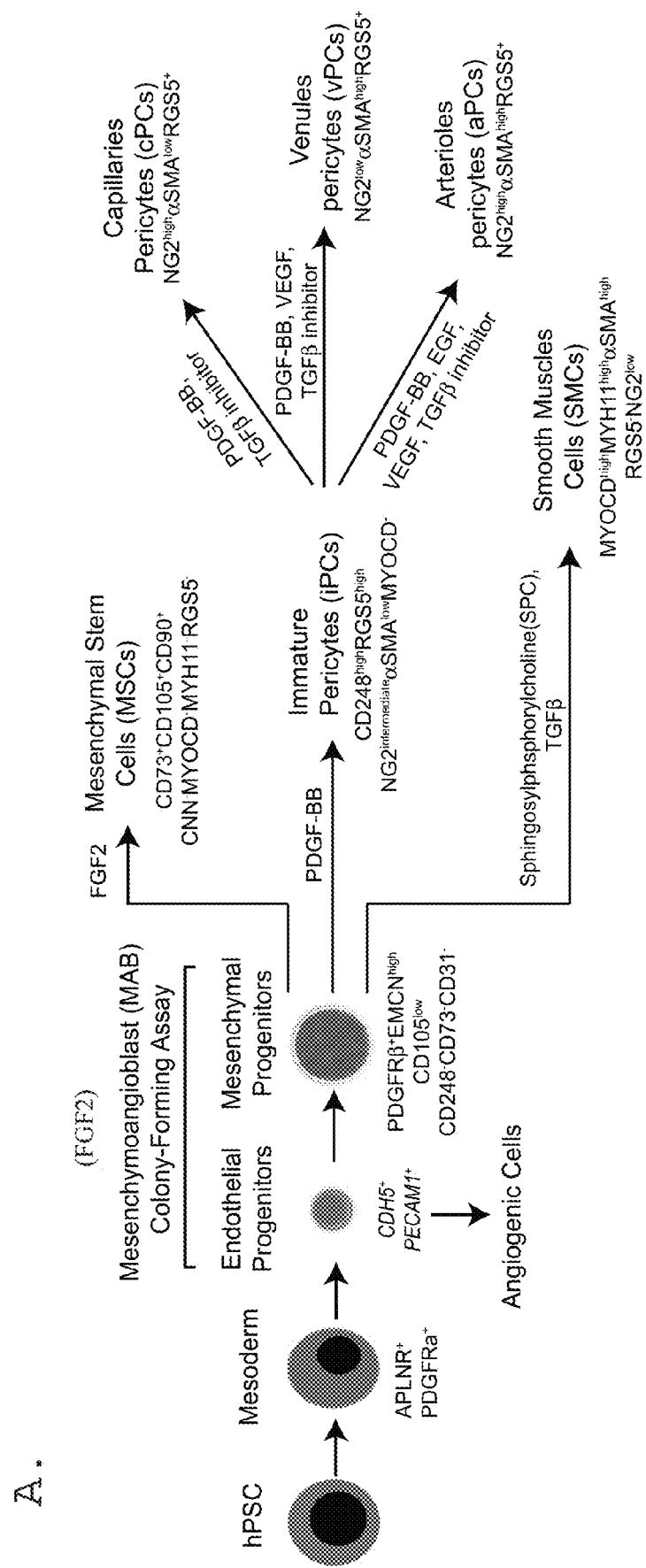
FIGS. 1A-1C provide schematic representations of methods for differentiating hPSCs into pericytes and smooth muscle cells. (A) hPSCs were differentiated on OP9 stromal cells for 2 days, then cultured in a semi-solid clonogenic medium in the presence of FGF2 to induce mesenchymoangioblast (MAB) colonies. The resulting MABs colonies were collected and cultured in mesenchymal medium with FGF2 to induce mesenchymal stem cells (MSCs), in pericyte medium containing PDGF-BB to induce immature pericytes (iPCs), or in smooth muscle growth medium containing sphingosylphosphorylcholine and TGFβ to induce smooth muscle cells (SMCs). The pericytes are further matured into capillary (cPCs), venous (vPCs), and arteriole (aPCs) pericytes. Cells were passaged when each culture reached 80-90% confluency. (B) For pericytes, MABs are expanded in a medium comprising PDGFBB. (C) For SMCs, MABs are expanded in a medium comprising sphingosylphosphorylcholine and TGFβ. MSCs also can be differentiated into SMCs in EGM™-2 Endothelial Cell Growth Medium-2 ("EGM2") medium comprising sphingosylphosphorylcholine and TGFβ. See also FIGS. 7A-7D.

Human pluripotent stem cells (hPSCs), either embryonic or induced, provide access to the earliest stages of human development and offer a platform on which to derive a large number of vasculogenic cells for cellular therapy and tissue engineering. The Inventors previously identified mesenchymoangioblasts (MABs) as a common precursor to the mesenchymal and endothelial lineages and as a source of mesoderm-derived mesenchymal stem cells (MSCs) in culture. Previously, MABs were referred to as mesangioblasts. See U.S. Patent Publication No. 2011/0236971, which is incorporated by reference herein as if set forth in its entirety. MABs arise within the APLNR+ subset of mesodermal precursor cells and can be specifically identified using a serum-free, FGF2-containing semisolid clonogenic medium. Under these conditions, MABs form colonies of mesenchymal progenitors that, in presence of FGF, give rise to MSCs having osteo-, chondro-, and adipogenic potential (FIG. 1A).

The present invention is based, at least in part, on the Inventors' discovery that mesenchymal progenitors also have a capacity to differentiate into vasculogenic cells: smooth muscle cells (SMCs) and pericytes (PCs). During embryonic development, a simple capillary network known as the primary capillary plexus is formed in the yolk sac by endothelial cell precursors. As development continues, the embryo's vasculature arises as a complex process of vascular remodeling occurs—a process that involves the proliferation and sprouting of new vessels from preexisting ones and recruitment of cells from the mesoderm and neural crest. During development and angiogenesis, SMCs and PCs are thought to play an important role in vascular remodeling and vessel stabilization. Blood vessels consist of an endothelial tube ensheathed by pericytes and SMCs. SMCs ensheath arteries, arterioles and veins. Pericytes ensheath endothelial cells found in microvessels, including capillaries, postcapillary venues, collecting venules, and pre-capillary arterioles. Arterioles have strong endothelial cell (EC) walls with dense layers of circumferentially oriented SMCs to withstand blood pressure. Capillaries are composed of endothelial cells that form the inner lining of the wall with a surrounding basal lamina and pericytes that extend long cytoplasmic processes over the surface of the vascular tube. Venules, like capillaries, have irregularly arranged pericytes with multiple cytoplasmic processes and are composed of thinner EC walls with valves to prevent backflow of blood. As described herein, the Inventors discovered that MAB-derived mesenchymal colonies can be induced to differentiate into vasculogenic cells when cultured in the presence of certain factors and demonstrated that MABs and mesenchymal progenitors have broader differentiation potential than initially recognized. MABs have the potential to provide all essential components of the vasculature for therapeutic vascular tissue engineering.

Accordingly, in one aspect, the present invention provides a method for obtaining a substantially pure population of vasculogenic cells (e.g., smooth muscle cells, pericytes). As used herein, the term "vasculogenic" refers to the ability of a cell, growth or signaling factor, or other biomolecule to contribute to, function in, or otherwise promote vasculogenesis or blood vessel development. Vasculogenesis generally refers to blood vessel development that involves the differentiation of certain progenitor cells into components of the vasculature. Vasculogenesis in vivo can involve circulating vascular progenitor cells which, in some cases, originate in the bone marrow. As used herein, the term "progenitor cell" refers to a cell that is not terminally differentiated in the cell lineage in interest and is capable of proliferating to give rise to a large number of cells that can in turn give rise to differentiated daughter cells. As used herein, the term "progenitor cell" also refers to a cell which is sometimes referred to in the art as a "stem cell" or a cell having higher potency than a differentiated cell. For example, the present invention provides methods of generating vasculogenic cells from mesenchymal progenitors.

As used herein, the term "substantially pure" refers to a population of cells that is at least about 75% (e.g., at least about 75%, 85%, 90%, 95%, 98%, 99% or more) pure, with respect to vasculogenic cells making up a total cell population. In other words, the term "substantially pure" refers to a population of vasculogenic cell of the present invention that contains fewer than about 20%, about 10%, or about 5% of non-pericytes when directing differentiation to obtain cells of the pericyte cell lineage, or non-smooth muscle cells when directing differentiation down the vascular smooth muscle cell lineage. The term "substantially pure" also refers to a population of vasculogenic cell of the present invention that contains fewer than about 20%, about 10%, or about 5% of non-vasculogenic cells in an isolated population prior to any enrichment, expansion step, or differentiation step. In some cases, a substantially pure isolated population of pericytes or smooth muscle cells generated according to a method provided herein is at least about 95% (e.g., at least about 95%, 96%, 97%, 98%, 99%) pure with respect to vasculogenic cells making up a total cell population.

In one embodiment, a method of the present invention comprises contacting a colony of mesenchymal progenitors to a culture medium comprising an effective amount of one or more factors that promote differentiation of the contacted mesenchymal progenitors to vasculogenic cells. In some cases, the colony of mesenchymal progenitors is derived from a mesenchymoangioblast (MAB). Previously, MABs were referred to as mesangioblasts. As depicted in FIG. 1A, MABs are mesodermal cells characterized by surface expression of apelin receptor (APLNR) that generate compact spheroid colonies under colony-forming, semi-solid culture conditions. MAB-derived colonies of mesenchymal progenitors comprise a uniform population of mesenchymal progenitors having a transcriptional profile representative of embryonic mesenchyme originating from lateral plate/extraembryonic mesoderm.

In some cases, a method of the present invention comprises generating a population of vasculogenic smooth muscle cells (SMCs) from a colony of mesenchymal progenitors such as, for example, a MAB-derived colony of mesenchymal progenitors. In exemplary embodiments, a mesenchymal progenitor comprises the following phenotype: PDGFRβ$^+$ (Platelet Derived Growth Factor Receptor β)/EMCN$^{high}$/CD105$^{low}$/CD248$^-$/CD73$^-$/CD31$^-$. EMCN (endomucin) is a mucin-like sialoglycoprotein that interferes with the assembly of focal adhesion complexes and inhibits interaction between cells and the extracellular matrix (Kinoshita et al., *FEBS Lett.* 2001 Jun. 15; 499(1-2):121-6).

The method can comprise directing differentiation along the smooth muscle cell lineage of vasculogenic cells by contacting a colony of mesenchymal progenitors to one or more instructive signals. For example, a MAB-derived colony of mesenchymal progenitors can be cultured in vitro in the presence of a culture medium comprising at least one of sphingosylphosphorylcholine (SPC) and Transforming Growth Factor Beta (TGFβ) in amounts effective to direct differentiation down the smooth muscle cell lineage (FIGS. 1A and 1C). SPC is a commercially-available bioactive lipid that mediates intracellular and extracellular signaling, and it is a ligand for endothelial differentiation gene receptor 3 (EDG3) (Okamoto et al., *Biochemical and Biophysical Research Communications* 260(1):203-208 (1999)). An effective amount of SPC can be an amount between about 2 μM and about 5 μM. In some cases, mesenchymal progenitors are cultured in the presence of a serum-free cell culture medium (e.g., M-SFEM) comprising SPC and one or more additional factors such as TGFβ. For example, a method of generating a population of SMCs can comprise culturing a MSC in a culture medium comprising about 2 μM-5 μM SPC and about 1 ng/mL-4 ng/mL TGFβ.

MAB-derived mesenchymal progenitors appropriate for use according to a method described herein can be derived from any source of pluripotent stem cells.

SMCs isolated and propagated according to a method provided herein express high levels of molecular markers for SMCs such as α-SMA (α-Smooth Muscle Actin; ACTA2), calponin, SM22 (Smooth muscle protein of 22 kDa), MYOCD (myocardin), and MYH11 (Myosin Heavy Chain 11). In addition, SMCs isolated and propagated according to a method provided herein display a strong contractile response to vasoconstrictors and can be identified by cell morphology and gene expression profiles.

In another aspect, the present invention relates to methods for generating pericytes. For example, a method of the invention can comprise generating a population of pericytes from mesenchymal progenitors (e.g., a colony of mesenchymal progenitors). Pericytes, also known as mural cells, ensheath blood microvessels (i.e., capillaries, arterioles, and venules) and are generally understood as having an organizational or structural role in angiogenesis. Multiple criteria including location, morphology, gene or protein expression patterns, and density around vessels are used to identify immature and mature pericytes. In general, a pericyte obtained according to a method provided herein can be identified based on expression of known pericyte molecular markers such as, without limitation, PDGFRβ, desmin (DES), CD13 (ANPEP; alanyl(membrane) aminopeptidase), α-SMA, RGS5 (Regulator of G-protein Signaling 5), NG2 (also known as CSPG4; chondroitin sulfate proteoglycan 4), CD248 (endosialin), ANG-1, CD146, CD44, CD90, and CD13.

In one aspect, the present invention provides a method of generating immature pericytes from mesenchymal progenitors. As used herein, the term "immature pericyte" refers to a proliferative pericyte having higher expression levels of PDGFRβ, DES, RGS-5, NG2, CNN1, TAGLN, and CALD1 than that observed in mesenchymal stem cells or MAB-derived mesenchymal progenitors (see, for example, FIG. 2 and FIG. 3). Immature pericytes also exhibit relatively high expression levels of CD248 and RGS5 and relatively low levels of NG2 and α-SMA as compared to mature pericytes (e.g., capillary pericyte, venule pericyte, and arteriole pericyte), but no or very low expression of MYOCD. In some cases, an isolated population of immature pericytes is obtained by contacting a colony of mesenchymal progenitors to Platelet-Derived Growth Factor-BB (PDGF-BB), which includes a homodimer of PDGF subunit B chains. For example, in some cases, a MAB-derived mesenchymal colony is cultured in vitro in medium that comprises an amount of PDGF-BB effective to direct differentiation of MSCs from contacted mesenchymal progenitors to the pericyte lineage. An effective amount of PDGF-BB to obtain an immature pericyte can be an amount between about 5 ng/mL and about 50 ng/mL. In some cases, such mesenchymal progenitors are cultured in vitro in the presence of a serum-free expansion medium (e.g., M-SFEM) comprising an effective amount of PDGF-BB.

In another aspect, the present invention provides methods for generating mature pericytes. The method can comprise culturing an immature pericyte such as, for example, an immature pericyte derived from a MAB-derived mesenchymal colony in the presence of a TGFβ receptor inhibitor and PDGF-BB (FIG. 1B). For example, an immature pericyte obtained according to a method of the present invention can be cultured in medium that comprises TGFβ receptor inhibitor and PDGF-BB in amounts effective to direct differentiation of an immature pericyte to one of the mature pericyte lineages. An amount of a TGFβ receptor inhibitor effective to obtain a mature pericyte can be an amount between about 2 μM and about 15 μM, and an effective amount of PDGF-BB can be an amount between about 5 ng/mL and about 50 ng/mL.

TGFβ receptor inhibitors appropriate for use in a method of the present invention include, without limitation, SB-431542, SB-525334, A83-01, LY2157299, LY210976, GW788388, RepSox, and SB-505124. For example, SB-431542, which is a commercially available chemical compound, is a potent inhibitor of the type I receptor (TGFβ Receptor I) and the activin receptor-like kinase receptors, ALK5, ALK4 and ALK7. See, e.g., Inman et al., *Mol. Pharmacol.* 62(1):65-74 (2002).

Capillary pericytes are obtained according to a method provided herein by culturing an immature pericyte in a culture medium (i.e., a maturation culture medium) comprising a TGFβ receptor inhibitor and PDGF-BB. In exemplary embodiments, a capillary pericyte maturation culture medium comprises about 10 μM SB-431542 and about 50 ng/mL PDGF-BB. Venule pericytes are obtained according to a method provided herein by culturing an immature pericyte in a medium comprising a TGFβ receptor inhibitor, PDGF-BB, and VEGF (Vascular Endothelial Growth Factor). In exemplary embodiments, a venule pericyte maturation culture medium comprises about 10 μM SB-431542, about 25 ng/mL PDGF-BB, and about 25 ng/mL VEGF. In some cases, arteriole pericytes are obtained according to a method provided herein that comprises culturing an immature pericyte in a pericyte medium comprising a TGFβ receptor inhibitor, PDGF-BB, VEGF, and EGF (Epidermal Growth Factor). In exemplary embodiments, a venule pericyte culture medium comprises about 10 μM SB-431542, about 10 ng/mL PDGF-BB, about 10 ng/mL VEGF, and about 5 ng/mL EGF2 (Epidermal Growth Factor-2). Differentiation of an immature pericyte into a mature pericyte cell type occurs following about 5 to about 7 days of culture in a medium described herein. In some cases, a base pericyte medium such as ScienCell Research Lab's Pericyte Medium (Catalog #1201) can be used. ScienCell's Pericyte Medium is a complete medium that promotes proliferation and growth of normal human vascular pericytes in vitro.

As described herein, mature pericytes obtained according to a method of present invention (e.g., capillary pericytes, venule pericytes, arteriole pericytes) can be identified by assaying for NG2, α-SMA expression, and/or RGS5 expression. Arteriole pericytes are $NG2^{high}/\alpha\text{-}SMA^{high}/RGS5^+$; venule pericytes are $NG2^{low}/\alpha\text{-}SMA^{high}/RGS5^+$; capillary pericytes are $NG2^{high}/\alpha\text{-}SMA^{low}/RGS5^+$.

Pericytes isolated and propagated as described herein typically demonstrate little contractile activity as compared to smooth muscle cells. As used herein, "isolating" and "isolated" refer to separating, selecting, or enriching for a cell type of interest or subpopulation of cells from surrounding, neighboring, or contaminating cells or from cells of another type.

In a further aspect, the present invention provides methods for obtaining an expanded population of vasculogenic cells relative to vasculogenic cells obtained by other means. For example, a method of present invention comprises obtaining an expanded population of smooth muscle cells. The method can comprise obtaining mesenchymal stem cells from a MAB-derived colony of mesenchymal progenitors, expanding the population of MSCs in vitro, and contacting the expanded MSC population to a culture medium comprising SPC and TGFβ, whereby smooth muscle cell differentiation is induced in the contacted MSCs. In some cases, a method of obtaining an expanded population of SMCs comprises culturing a mesenchymal stem cell colony in a culture medium with FGF2 to obtain mesenchymal stem cell lines and culturing mesenchymal stem cells in a culture medium comprising effective amounts of SPC and TGF-β under conditions that promote differentiation of an expanded population of mesenchymal stem cells into an expanded population of SMCs. An expanded population of smooth muscle cells obtained according to a method described herein is useful for, among other things, vascular tissue engineering and therapeutic applications. Since SMCs cannot be expanded in vitro using other methods, the methods of the present invention are advantageous for obtaining greatly expanded populations of smooth muscle cells. In some cases, the methods additionally make it possible to obtain commercially useful quantities of SMCs for various commercial and clinical applications.

In exemplary embodiments, vasculogenic populations obtained according to methods described herein comprise expanded populations of SMCs. Pericytes and vascular smooth muscle cells derived according to a method provided herein can be used in a wide range of clinical applications. These vasculogenic cells also can be used as raw materials for creating blood vessels in vitro or in vivo. Such vessels will be useful, for example, in revascularizing damaged tissues and in treating peripheral artery disease. Engraftment of and vasculogenesis by externally injected cells has been shown by in vivo animal studies. See, for example, Kim et al., *J. Am. Coll. Cardiol.* 56: 593-607 (2010).

In a further aspect, therefore, the present invention provides methods and compositions for cell transplantation, cell replenishment, and cell or tissue replacement. The method can comprise providing to a subject in need thereof a therapeutically effective amount of vasculogenic cells derived according to a methods provided herein, whereby providing vasculogenic cells treats the subject. Disorders requiring cell or tissue replacement and improved vasculogenesis include, without limitation, myocardial and peripheral vascular ischaemia, other peripheral artery diseases, myocardial infarction (MI), stroke, and diabetic neuropathy, and any other disorder or disease for which the stricken individual would benefit from angiogenic regenerative medicine. Vasculogenic cell transplantation according to a method provided herein can also be useful for treatment of damaged skeletal muscle and bone. Preferred individual subjects according to the present invention are mammals including, without limitation, humans and non-human primates, as well as canines, felines, ovines, porcines, equines, and bovines. In some cases, a MAB-derived colony of mesenchymal progenitors is obtained using a pluripotent cell (e.g., an induced pluripotent stem cell) derived from the subject in need of treatment. However, MAB-derived mesenchymal progenitors also can be obtained using pluripotent stem cells of, preferably, a syngeneic or allogeneic donor. Less preferably, a xenogeneic donor is used.

A treatment method of the present invention can comprise transplanting the vasculogenic cells into the recipient subject. This is generally effected using methods well known in the art, and usually involves directly injecting or otherwise introducing vasculogenic cells into the subject using clinical tools known to those skilled in the art (e.g., U.S. Pat. Nos. 6,447,765; 6,383,481; 6,143,292; and 6,326,198). For example, introduction of vasculogenic cells of the present invention can be effected locally or systematically via intravascular administration, such as intravenous or intra-arterial administration, intraperitoneal administration, and the like. Cells can be injected into an infusion bag (e.g., 50 mol Fenwall infusion bag) using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

In exemplary embodiments, vasculogenic cells of the present invention are provided to the subject as a pharmaceutical composition comprising the cells and one or more pharmaceutically acceptable carriers, buffers, or excipients. The pharmaceutical composition for administration must be formulated, produced, and stored according to standard methods that provide proper sterility and stability. A pharmaceutical composition of the present invention may also comprise one or more growth factors or cytokines (e.g., angiogenic cytokines) that promote the survival or engraftment of transplanted cells, promote angiogenesis, modulate the composition of extracellular or interstitial matrix, and/or recruit other cell types to the site of transplantation.

After administering the cells into the subject, the effect of the treatment method may be evaluated, if desired, as known in the art. The treatment may be repeated as needed or required.

Each document cited herein is incorporated by reference herein as if set forth in its entirety. Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1—Obtaining Pericytes and Smooth Muscle Cells from Human ESCs and iPSCs Experimental Procedures Maintenance and Differentiation of Human ESCs and iPSCs: Human ESC (H1) line (Thomson et al., *Science* 282:1145-47 (1998)) and iPS-DF19-9-7T were obtained from WiCell Research Institute. H9-EGFP (Xia et al., *Stem Cells* 26(2):523-533 (2008)) was kindly provided by Su-Chun Zhang (University of Wisconsin, Madison, WI). All PSCs were maintained in an undifferentiated state on irradiated mouse embryonic fibroblasts as described (Amit et al., *Stem Cell Reviews & Reports* 6(2):248-59 (2010); Yu et al., *Science* 318(5858):1917-1920 (2007)). Mouse OP9 bone marrow stromal cell line was provided by Tom Nakano (Osaka University). Human pluripotent stem cells were induced to differentiate in co-culture with OP9 stromal cells and were depleted of OP9 cells using anti-mouse CD29 antibodies (AbD Serotec) as previously described (Vodyanik et al., *Blood* 105(2):617-26 (2005); Vodyanik and Slukvin, *Curr. Protoc. Cell Biol.*, John Wiley & Sons, Inc. Unit 23.6 (2007)). According to an alternative protocol, MABs were generated under completely defined conditions as described in U.S. application Ser. No. 14/206,778, filed Mar. 12, 2014, which is incorporated by reference herein as if set forth in its entirety.

Colony-Forming Culture for Mesenchymoangioblasts (MABs): Human PSCs were differentiated on OP9 for 2 days and MABs were generated as described (Vodyanik et al., *Cell Stem Cell* 7(6):718-29 (2010)). Briefly, a single-cell suspension of differentiated hPSCs derived cells was prepared at $0.5$-$2 \times 10^4$ cells/mL in a semisolid colony-forming serum-free medium (CF-SFM) containing 40% ES-Cult M3120 methylcellulose (2.5% solution in Iscove's modified Dulbecco's medium; Stem Cell Technologies), 25% STEMSPAN® serum-free expansion medium (StemSpan™ SFEM; StemCell Technologies), 25% human endothelial serum-free medium (ESFM®; Invitrogen), 10% BIT 9500 supplement (Stem Cell Technologies), GLUTAMAX® (1/100 dilution; Invitrogen), Ex-Cyte supplement (1/1000 dilution; Millipore), 100 µM monothioglycerol (MTG), 50 µg/mL ascorbic acid, and 20 ng/mL basic fibroblast growth factor (FGF2). Individual mesenchymal colonies were picked from culture on day 12 under an inverted microscope. For bulk collection of mesenchymal colonies (>100 µm in diameter), colony-forming cultures from day 12 were diluted 1/5 in Dulbecco's modified Eagle's medium/F12 medium and filtered through 100 µm cell strainers (BD Biosciences).

Colony-Derived Immature Pericytes: Individual or multiple mesenchymal colonies collected by filtration (>100 colonies per culture) were plated on a fibronectin (5 µg/mL; Invitrogen)+collagen-coated (10 µg/mL; Stem Cell Technologies) plate in mesenchymal serum-free expansion medium (M-SFEM) comprising 50% STEMLINE II® serum-free HSC expansion medium (HSFEM; Sigma), 50% ESFM, GLUTAMAX® (1/100 dilution), Ex-Cyte supplement (1/2000 dilution), 100 µM MTG, 10 ng/mL FGF2, and 50 ng/mL PDGF-BB. After 4 days, attached colonies were dissociated by STEMPRO® ACCUTASE® solution (Invitrogen) and plated on the fibronectin- and collagen-coated plates in a pericyte medium (ScienCell Research Laboratories, CA, USA) for 14 days. Colony-derived pericyte lines established either from individual (clonal lines) or multiple (polyclonal lines) colonies were routinely maintained by 3 day subculture on fibronectin- and collagen-coated plates in pericyte medium and passaged using STEMPRO® ACCUTASE® detachment solution. The first confluent culture obtained after 14 days of culture was denoted as passage 1.

According to an alternative protocol, immature pericytes were also generated directly from MABs using a mesenchymal colony-forming culture medium having 5-15 ng/mL of PDGF-BB and about 20 ng/ml FGF2 (FIG. 1B). Briefly, a single-cell suspension of differentiated hPSC-derived MABs was prepared at $0.5$-$2 \times 10^4$ cells/mL in a semisolid, serum-free mesenchymal colony-forming culture medium (CF-SFM): 40% ES-Cult M3120 methylcellulose (2.5% solution in Iscove's modified Dulbecco's medium; Stem Cell Technologies), 25% STEMSPAN® serum-free expansion medium (SFEM; Stem Cell Technologies), 25% human endothelial serum-free medium (ESFM; Invitrogen), 10% BIT 9500 supplement (Stem Cell Technologies), GLUTAMAX® (1/100 dilution; Invitrogen), Ex-Cyte supplement (1/1000 dilution; Millipore), 100 µM monothioglycerol (MTG), 50 µg/mL ascorbic acid, and 20 ng/mL basic fibroblast growth factor (FGF2) and PDGF-BB (10 ng/mL) (FIG. 1B). Mesenchymal progenitors generated in the presence of PDGF-BB were collected and plated on fibronectin- and collagen-coated plates in M-SFEM or pericyte medium (available from ScienCell Research Laboratories, CA, USA). After 3 days, attached colonies were dissociated using STEMPRO® ACCUTASE® detachment solution (Invitrogen) and plated on fibronectin- and collagen-coated plates in M-SFEM. The established pericyte lines were routinely maintained using 3 day subculture on fibronectinand collagen-coated plates in M-SFEM or pericyte medium using STEMPRO® ACCUTASE® detachment solution.

For maturation, iPCs were cultured in pericyte medium containing SB-431542 (10 μM)+PDGF-BB (50 ng/ml), SB-431542 (10 μM)+PDGF-BB (25 ng/ml)+VEGF (25 ng/ml), and SB-431542 (10 μM)+PDGF (10 ng/ml)+VEGF (10 ng/ml)+EGF2 (5 ng/ml) for approximately 6 additional days to generate capillary pericytes (cPCs), venule pericytes (vPCs), and arteriole pericytes (aPCs), respectively.

Colony-derived SMC lines: Individual or multiple mesenchymal colonies collected by filtration (>100 colonies per culture) were plated on human collagen I (10 μg/ml; BD bioscience) coated plates in smooth muscle growth medium (ScienCell Research Laboratories, CA, USA) containing Sphingosylphosphorylcholine (2 μM) and TGFβ (1 ng/ml). After 6 days, the attached colonies were dissociated by STEMPRO® ACCUTASE® detachment solution (Invitrogen) and cultured on plates coated with human collagen I (10 μg/ml) in smooth muscle growth medium (ScienCell Research Laboratories, CA, USA) for 21 days. The SMCs were further matured by culturing for an additional 12 days on human collagen I (10 μg/ml) coated plates in DMEM medium.

Differentiation of SMCs from MSCs: SMCs were also differentiated from mesenchymal stem cells (MSCs) by culturing in EGM™-2 Endothelial Cell Growth Medium-2 ("EGM2") (Lonza Walkersville, Inc.) medium with sphingosylphosphorylcholine (SPC, 2 μM) and TGFβ (2 ng/ml) for 3 weeks. The identity of SMCs was verified by immunostaining for smooth muscle actin (1:100), Myosin Heavy Chain 11 (1:300) and calponin (1:1000) by immunostaining. The immunostained cells were examined using Nikon Eclipse Ti-E confocal system (Nikon Instruments Inc. Melville, NY).

Fluorescence Activated Cell sorting (FACS) analysis: Phenotypic characterization of cells was performed using flow cytometry following labeling with antibodies (Table 1) as previously described (Vodyanik et al., Cell Stem Cells 7(6):718-29 (2010)). 7-aminoactinomycin D (7-AAD) was used to exclude dead cells. Cells were analyzed using a FACSCalibur™ flow cytometer (BD Biosciences).

Immunofluorescence: Cells were fixed with 4% paraformaldehyde for 15 minutes, washed with phosphate buffered saline (PBS), permeabilized with a solution of 0.1% Triton-X (Sigma) for ten minutes, washed with PBS, and incubated overnight with anti-human SMA (1:100; Abcam), anti-human NG2 (1:100; eBioscience), anti-human MYH11 (1:300; Abcam), anti-human Calponin (1:1000), and anti-human Desmin (1:1000). Cells were washed five times with PBST and incubated with anti-mouse Alexa 555 conjugated (1:1000; Secondary antibodies, Invitrogen) or anti-rabbit IgG Alexa Fluor 488 conjugate (1:1000; Secondary antibodies, Invitrogen) for one hour, washed with PBST, and incubated with DAPI (1:1000; Sigma-Aldrich, USA) for 10 minutes. The immunolabeled cells were examined using Nikon Eclipse Ti-E confocal system (Nikon Instruments Inc. Melville, NY).

Quantitative Real-Time PCR: Total RNA was extracted from pericytes, SMCs, and MSCs using RNeasy mini Kit (Qiagen). cDNA synthesis was carried out using Advantage RT-for-PCR Kit (Clontech). Quantitative real-time PCR analysis was performed for all the cDNA samples using specific primers (Table 2) and Fast SYBR Green qPCR SuperMix UDG kit (Invitrogen). The reactions were run on a Mastercycler realplex thermal cycler (Eppendorf) and expression levels were calculated by minimal cycle threshold values (Ct) normalized to the reference expression of GAPDH in each sample (Pfaffl, Nuc. Acids Res. 29(9):e45 (2001)).

RNA-Seq Analysis: Total RNA was isolated from the subpopulation cells using RNeasy mini Kit (Qiagen). Total RNA was quantified using the Life Technologies Qubit fluorometer (Q32857) and the Agilent Bioanalyzer 2100. Samples were then prepared for sequencing using the Illumina TruSeq RNA Sample Preparation Kit v2 (RS-122-2001), according to the manufacturer's protocol. Final sample libraries were quantified with the Life Technologies Qubit fluorometer and sequenced on the Illumina HiSeq 2500 (SY-401-1003-PRE). Base-calling and demultiplexing were done with the Illumina Genome Analyzer Casava Software, version 1.8.2. After quality assessment and filtering for adapter molecules and other sequencing artifacts, the remaining sequencing reads were aligned to 19084 RefSeq genes extracted from the Illumina iGenomes annotation, selecting only "NM_" designated genes. Bowtie v 0.12.9 was used, allowing two mismatches in a 28 bp seed, and excluding reads with more than 200 alignments (Langmead et al., Genome Biology 10(3):R25 (2009)). RSEM v 1.2.3 was used to estimate isoform or gene relative expression levels in units of "transcripts per million" (tpm) (Li and Dewey, BMC Bioinformatics 12:323 (2011); Li et al., Bioinformatics 26(4):493-500 (2010)).

In vitro Angiogenesis and Binding Assay: For the tube formation assay, human umbilical cord endothelial cells (HUVECs, $3 \times 10^4$ cells/well) were co-seeded with H9-EGFP-derived cells (MSCs, SMCs or pericytes, $1.5 \times 10^4$ cells/well) on pre-solidified Matrigel (BD Bioscience, USA) in EGM2 media. The cells were incubated for different time point at 37° C., 5% $CO_2$ in a humidified atmosphere. Vascular network was photographed at the indicated time point using a Nikon Eclipse Ti-E configured with an MR confocal system (Nikon Instruments Inc. Melville, NY) and quantified using Wimasis tube analysis software (Wimasis Gmbh, Germany).

Gel Contraction Assay: Ligand-induced cell contractility was assessed by a gel contraction assay, performed as previously described (Dallot et al., Biol Reprod 68:937-942 (2003)). Briefly, 8 volumes of type I collagen solution (3 mg/mL)(BD Bioscience, USA) was mixed with 1 volume of 10×DMEM and 1 volume of 0.1 N NaOH on ice to yield 2 mg/mL of collagen solution at pH 7.4. A cell suspension was made in the collagen solution on ice ($5 \times 10^5$ cells/mL) and incubated at 37° C. for 2 hours to allow for gelling, followed by the addition of medium over the gel. After allowing the cells to spread within the gel overnight, the gels were gently detached and lifted from the bottom of the well. 100 μM of carbachol (Cbchl) was administered and the cells were photographed after 48 hours. The area of the gel lattices was determined with ImageJ software (NIMH, Bethesda, MD), and the relative lattice area was obtained by dividing the area at particular time points by the initial area of the lattice, and then graphed.

Time-Lapse Imaging: Cbch1 (100 µM) was added to the monolayer of MSCs, pericytes or SMCs derived from H9-GFP. Time lapse images were recorded for 15 minutes following Cbch1 addition using Nikon Eclipse Ti-E configured with an MR confocal system, motorized stage (Nikon Instruments Inc. Melville, NY), and Tokai-Hit Stage Top Incubator (Tokai Hit CO., Ltd., Shizuoka-ken, Japan) at 37° C. and 5% $CO_2$. Images were acquired continuously using Nikon Elements (NIS—element C) imaging software with CFI Plan Fluor DLL 20×NA 0.5 WD 2.1 MM objective (Nikon Instruments Inc. Melville, NY). The time-lapse serial images were converted to Quick-time movies (.mov). Quantification of the percentage of contractile cells was measured by using ImageJ software (NIMH, Bethesda, MD). The percentage of contracting cells was determined from 5 different optical fields. Similarly, time-lapse imaging was also performed for tube formation assay where HUVECs were co-seeded with H9-EGFP-derived iPCs or SMCs on pre-solidified Matrigel (BD Bioscience, USA) in EGM2 media (Promocell, Heidelberg, Germany) and images were acquired at 10 minute intervals for 24 hours.

Matrigel-Fibrin Matrix Implants: HUVECs were mixed with h9ESC-GFP derived MSCs, pericytes, or SMCs (2:1) in 500 µl Matrigel (growth factor reduced; BD Biosciences) and fibrinogen (final concentration 2 mg/ml; Calbiochem) containing different growth factors (250 ng/ml each of VEGF and bFGF). Thrombin (0.4 U; Calbiochem) was added to the mixture and injected subcutaneously on each side lateral to the abdominal midline region into 8-10 weeks old NOD-SCID mice. Mice were euthanized after 2 weeks of implantation and constructs were retrieved. The implants were fixed overnight in 10% neutral buffered formalin, embedded in paraffin, sectioned, and then stained with human anti-CD31 and anti-GFP antibodies.

Statistical Analysis: Statistical analysis was performed using GraphPad Software (La Jolla, CA, USA). Data obtained from multiple experiments were reported as the mean±SE. The significance of difference between the mean values was determined by paired Student t test. Differences were considered significant when $p<0.01$.

TABLE 1

| | | Antibodies | | |
|---|---|---|---|---|
| Antigen | Fluoro-chrome-conjugated | Clone | Source | Catalog No. |
| CD13 | FITC | 123H1 | BD Bioscience | M101-4 |
| CD31 | FITC | WM59 | BD Bioscience | 555445 |
| CD34 | PE | 8G12 | BD Bioscience | 348057 |
| CD45 | APC | HI30 | BD Bioscience | 555485 |
| CD73 | PE | AD2 | BD Biosciences | 550257 |
| CD90 | APC | 5E10 | BD Biosciences | 559869 |
| CD105 | PE | SN6 | CALTAG | MHCD10504 |
| CD146 | PE | P1H12 | BD Biosciences | 550315 |
| APLNR | APC | 72133 | R&D Systems | FAB856A |
| PDGFRβ | PE | 28D4 | BD Bioscience | 558821 |
| NG2 | None | Polyclonal | eBioscience | 14-6504 |
| NG2 | None | Polyclonal | Millipore | MAB5384 |
| ASMA | None | 1A4 | Abcam | Ab7817 |
| MYH11 | None | SMMS-1 | Abcam | ab106919 |
| Calponin | None | CALP | Thermo Scientific™ | MS-1168-PO |
| Desmin | None | Polyclonal | Thermo Scientific™ | Rb-9014-PO |

TABLE 2

| | qRT-PCR Primers | |
|---|---|---|
| Gene | Direction | Sequences |
| ASMA | Forward | 5' GTG TTG CCC CTG AAG AGC AT 3' (SEQ ID NO: 1) |
| | Reverse | 5' GCT GGG ACA TTG AAA GTC TCA 3' (SEQ ID NO: 2) |
| NG2 | Forward | 5' GTC TTT TGA GGC TGC CTG TC 3' (SEQ ID NO: 3) |
| | Reverse | 5' CTG TGT GAC CTG GAA GAG CA 3' (SEQ ID NO: 4) |
| PDGFRβ | Forward | 5' TGC AGC ACC ACT CCG ACA AGC 3' (SEQ ID NO: 5) |
| | Reverse | 5' TCG CTC TCC CCG GTC AAG GAC 3' (SEQ ID NO: 6) |
| Caldesmon | Forward | 5' CTG GCT TGA AGG TAG GGG TTT 3' (SEQ ID NO: 7) |
| | Reverse | 5' TTG GGA GCA GGT GAC TTG TTT 3' (SEQ ID NO: 8) |
| RGS5 | Forward | 5' TCC AGG GAA TCA CGC CAC TGC 3' (SEQ ID NO: 9) |
| | Reverse | 5' AGC CAG ACT CAG TTG GTG ACC T 3' (SEQ ID NO: 10) |
| MYCOD | Forward | 5' AAG CGC CAT CTC TTG AGG TA 3' (SEQ ID NO: 11) |
| | Reverse | 5' GCG CCT TTA TTT TGA CC 3' (SEQ ID NO: 12) |
| MYH11 | Forward | 5' GGA GGA TGA GAT CCT GGT CA 3' (SEQ ID NO: 13) |
| | Reverse | 5' TTA GCC GCA CTT CCA GTT CT 3' (SEQ ID NO: 14) |
| Calponin | Forward | 5' CAA CCA CCA CGC ACA CAA CTA C 3' (SEQ ID NO: 15) |
| | Reverse | 5' GGT CCA GCC AAG AGC AGC AG 3' (SEQ ID NO: 16) |
| VE-cadherin | Forward | 5' GAT CAA GTC AAG CGT GAG TCG 3' (SEQ ID NO: 17) |
| | Reverse | 5' AGC CTC TCA ATG GCG AAC AC 3' (SEQ ID NO: 18) |

Results

Figures 1A, 1B, 1C:
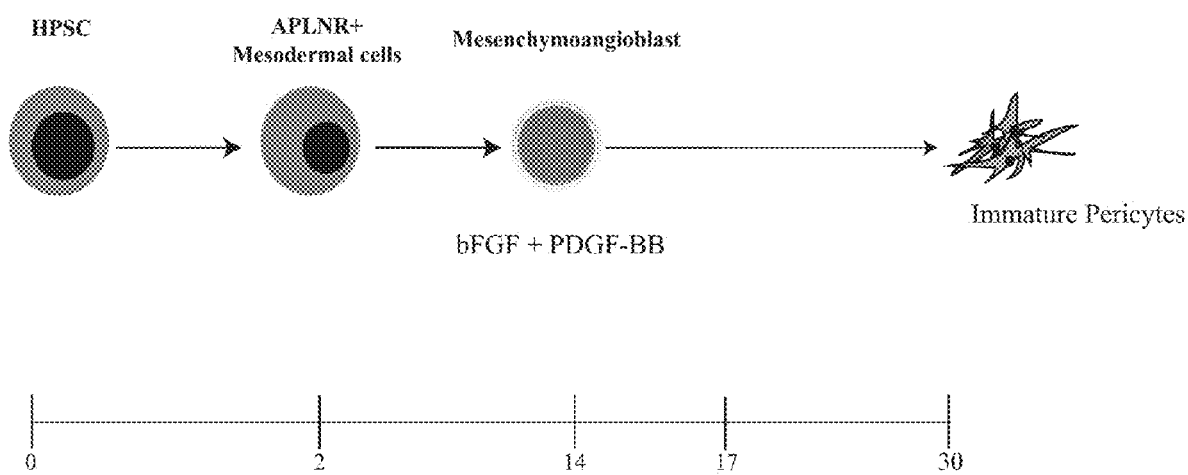
Figures 1A, 1B, 1C:
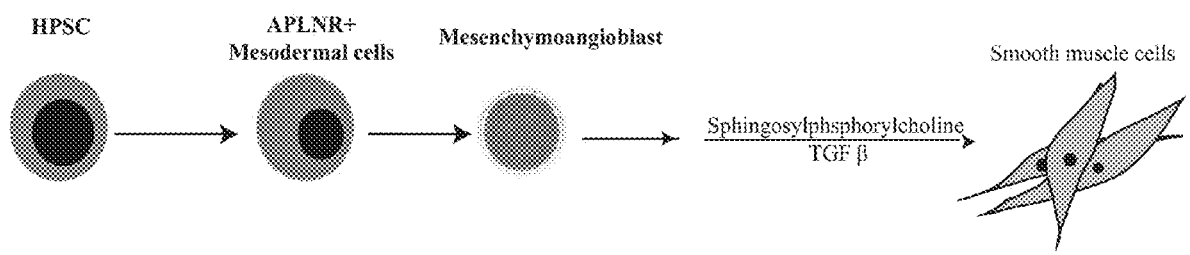

Induction and specification of pericytes from MABs: As we previously showed, hPSCs co-cultured with OP9 for 2-3 days acquire transient potential to form FGF2-dependent compact colonies with a MSC and endothelial cell potential that define MABs (Vodyanik et al., Cell Stem Cells 7(6): 718-29 (2010)). As shown in FIG. 1, these mesenchymal colonies arise from APLNR$^+$/PDGFRA$^+$ primitive mesodermal cells expressing T, MIXL1, EOMES and MESP1 primitive streak genes and FOXF1, GATA2, and HAND1 genes associated with lateral plate mesoderm development. Kinetic analysis of the endothelial and MSC potential and time-lapse studies revealed that the development of MAB colonies in clonogenic medium proceed through core stages at which APLNR$^+$/PDGFRA$^+$ cells form clusters of tightly packed CDH5− and CD31− (platelet endothelial cell adhesion molecule [PECAM]) expressing cells with angiogenic potential. Subsequently, core-forming cells undergo endothelial-mesenchymal transition giving rise to mesenchymal cells, which form a shell around the core developing into a mature MAB colony. Molecular profiling and phenotypic analysis revealed that MAB colonies are composed of Endomucin (EMCN)$^{high}$CD105$^{low}$/CD248$^-$CD73$^-$CD31$^-$ mesenchymal progenitor cells with transcriptional profile representative of embryonic mesenchyme derived from lateral plate mesoderm. When transferred to adherent serum-free cultures, MAB colonies gave rise to CD73$^+$CD105$^+$CD31$^-$CD45$^-$ MSC lines with osteo-, chondro-, and adipogenic differentiation potentials (Vodyanik et al., Cell Stem Cells 7(6):718-29 (2010)).

Figures 7A, 7B, 7C, 7D:
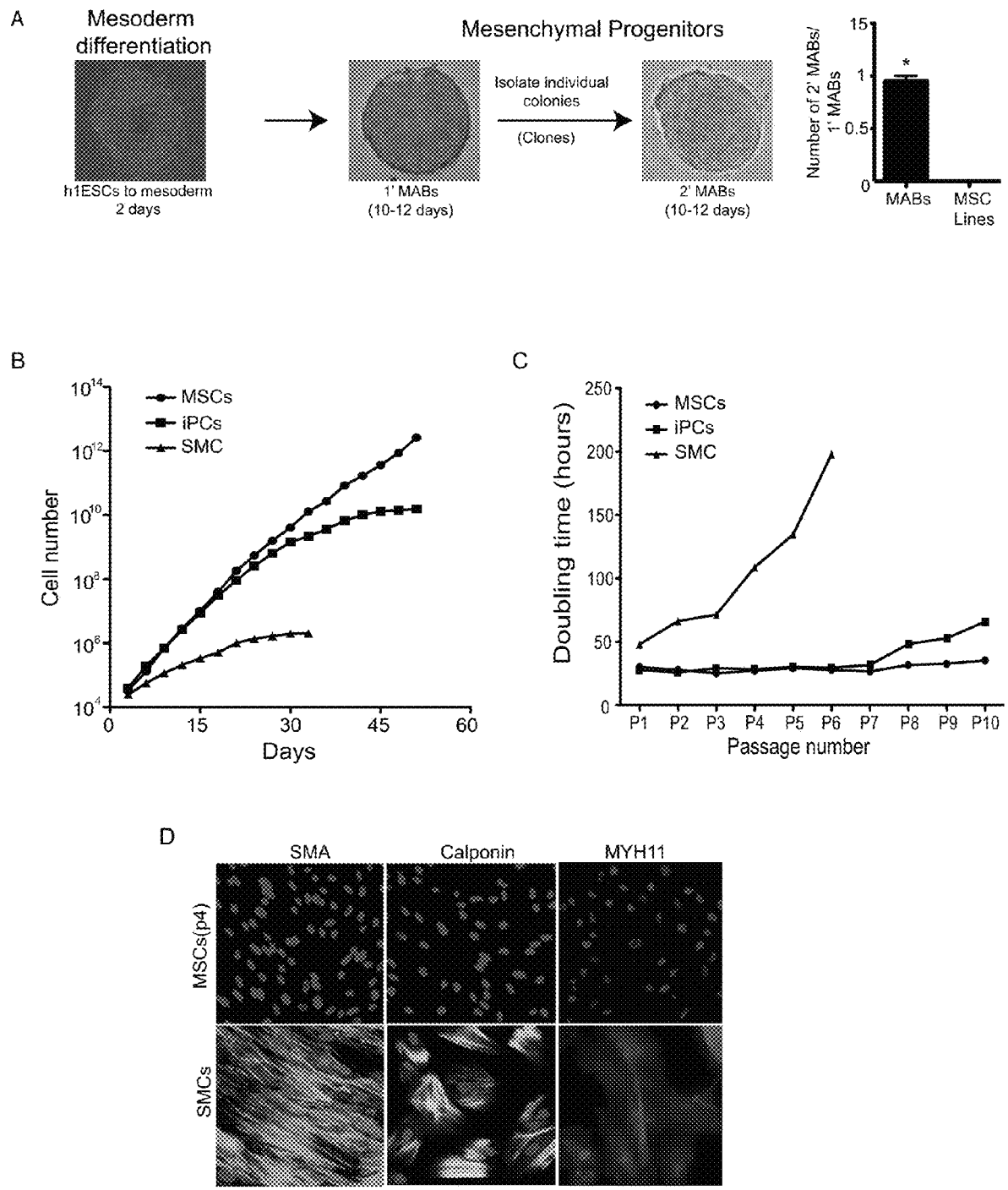
FIGS. 7A-7D are a series of images and graphs demonstrating the self-renewal and expansion potential of MABs and vasculogenic cells. (A) Single cell suspension was made from individual MAB colony and placed into secondary CF-SFM medium to assess the self renewal potential of MAB colonies. Phase contrast images show primary and secondary MAB colonies. (B) Graph shows MSC, SMC, and iPC cell proliferation over several weeks. (C) Graph shows the doubling potential of MSCs and vasculogenic cells over several passages. (D) MSCs (passage 4) differentiated to SMCs in EGM2 medium containing sphingosylphosphorylcholine+TGFβ. Panels show immunostaining for smooth muscle cell markers SMA, MYH11, and calponin.

To confirm that MAB-derived mesenchymal colonies comprise progenitor cells with self-renewal properties, we evaluated their potential to generate secondary MAB colonies after replating in semisolid clonogenic medium. As shown in FIG. 7A, single cell suspensions from the bulk of MAB colonies were capable of giving rise to secondary MAB colonies in a semi-solid clonogenic medium, thus indicating that MAB colonies contain progenitors capable of self-renewal. In contrast, MSC lines generated from MAB colonies completely lost clonogenic potential in semi-solid medium.

Figures 2A, 2B, 2C, 2D:
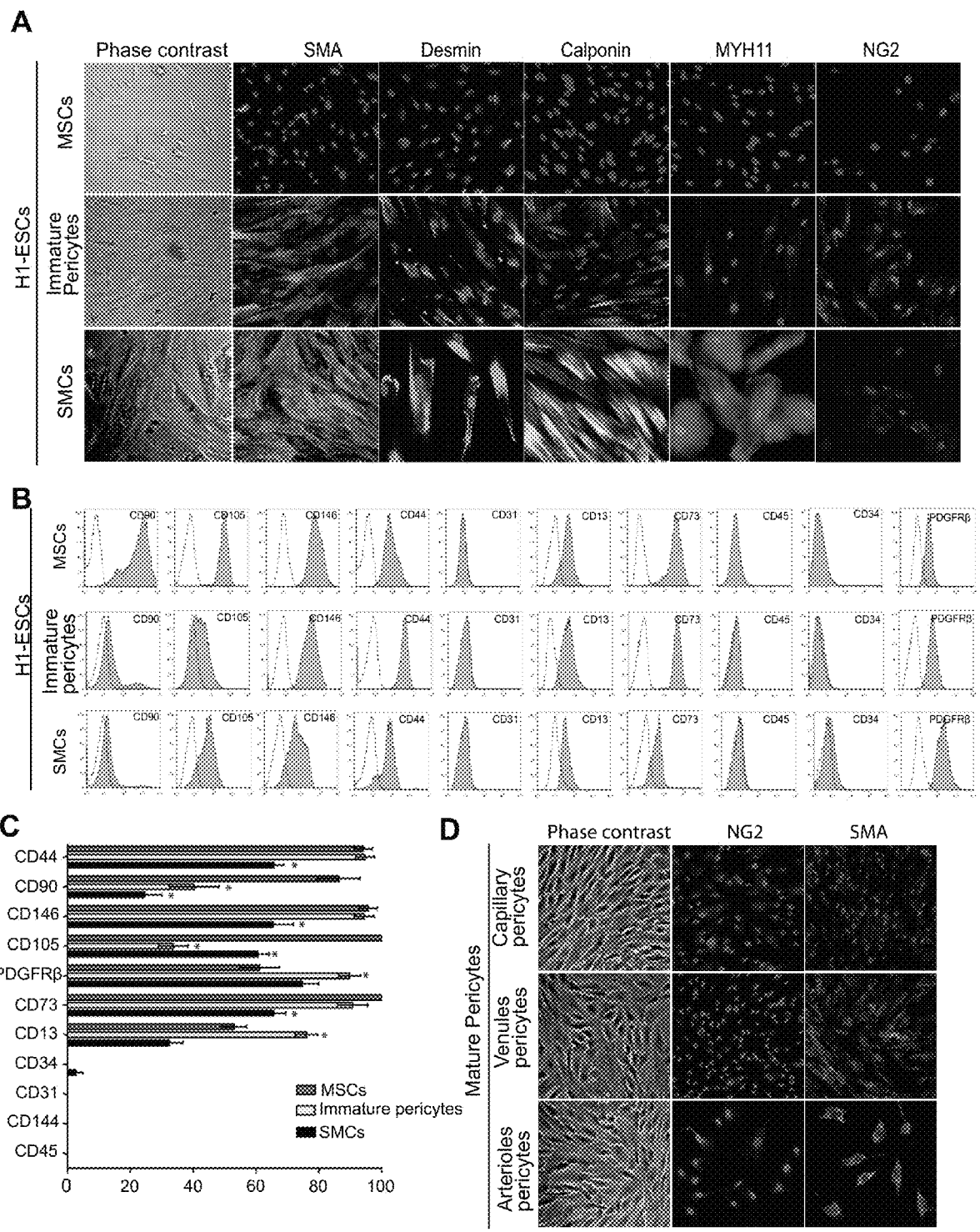
FIGS. 2A-2D present data characterizing iPCs and SMCs derived from hPSCs. (A) Immunohistochemical staining of MSCs, iPCs and SMCs derived from H1 hESCs for smooth muscle actin (SMA), desmin, calponin, MYH11, and NG2. Nuclei (blue) were stained with DAPI. (B) Phenotypic characterization of MSCs, iPCs, and SMCs by flow cytometry. (C) Summary of phenotype of iPCs and SMCs, as detected by flow cytometry. Results are displayed as mean±SE of three independent experiments (*p<0.01). (D) iPCs were maturated to achieve three distinct phenotypes of pericytes namely capillary, venule, and arteriole pericytes. Three distinct phenotype were confirmed by immunohistochemistry to detect expression of two markers: NG2 and SMA. Representative results from three independent experiments are shown. Bar=100 μm.
Figures 3A, 3B:
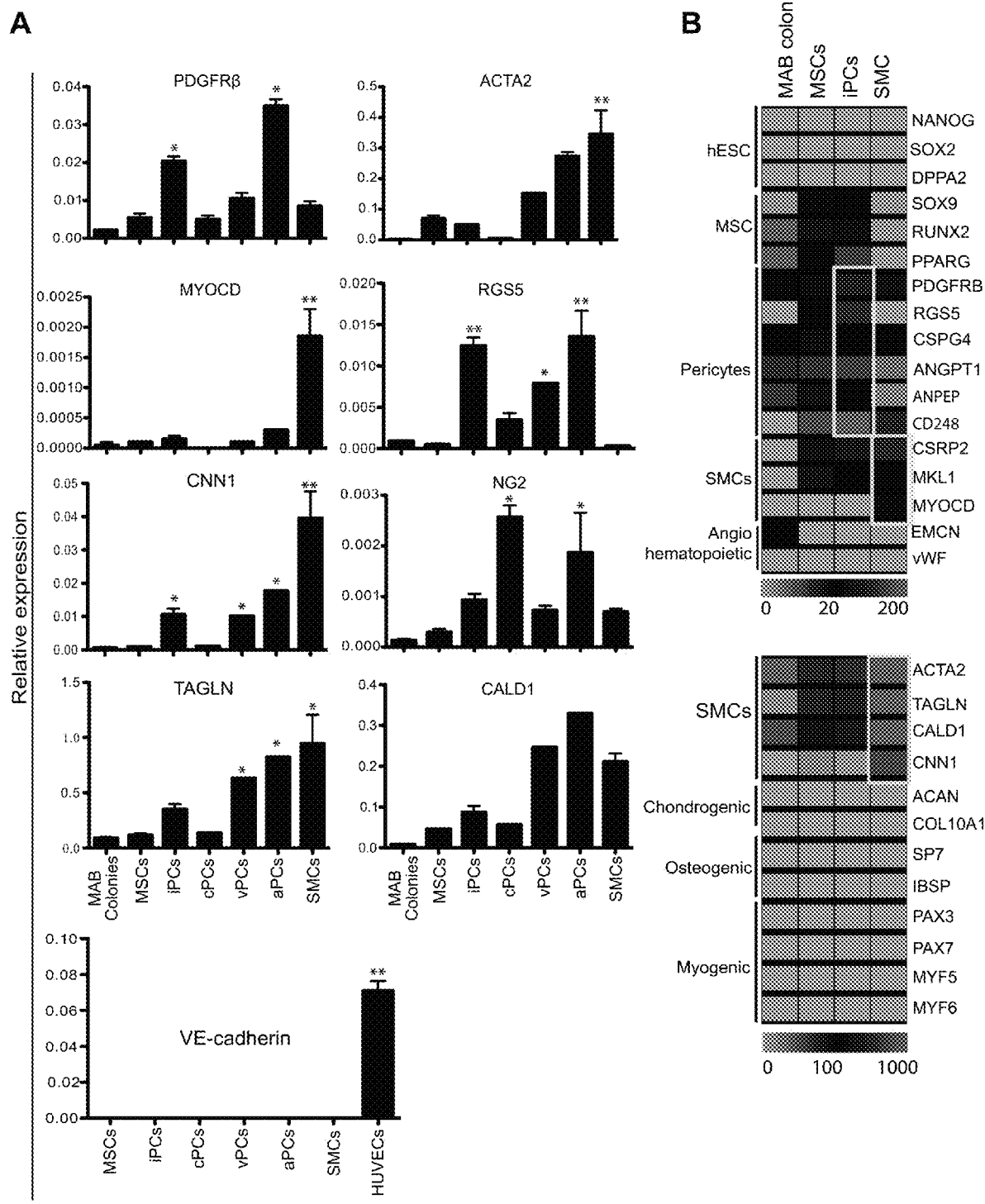
FIGS. 3A-3B present data from gene expression profiling of MAB colonies, MSCs, iPCs, and SMCs. (A) MSCs, iPCs, and SMCs specific gene expression as measured by qRT-PCR. Values of mRNA levels normalized to GAPDH levels. Results are mean±SE of three independent experiments (**p<0.001, *p<0.01). HUVECs were used as a negative control. (B) Heat map to show the expression of selected genes as determined by RNAseq. The gene expression levels are estimated in terms of "transcripts per million."
Figure 8:
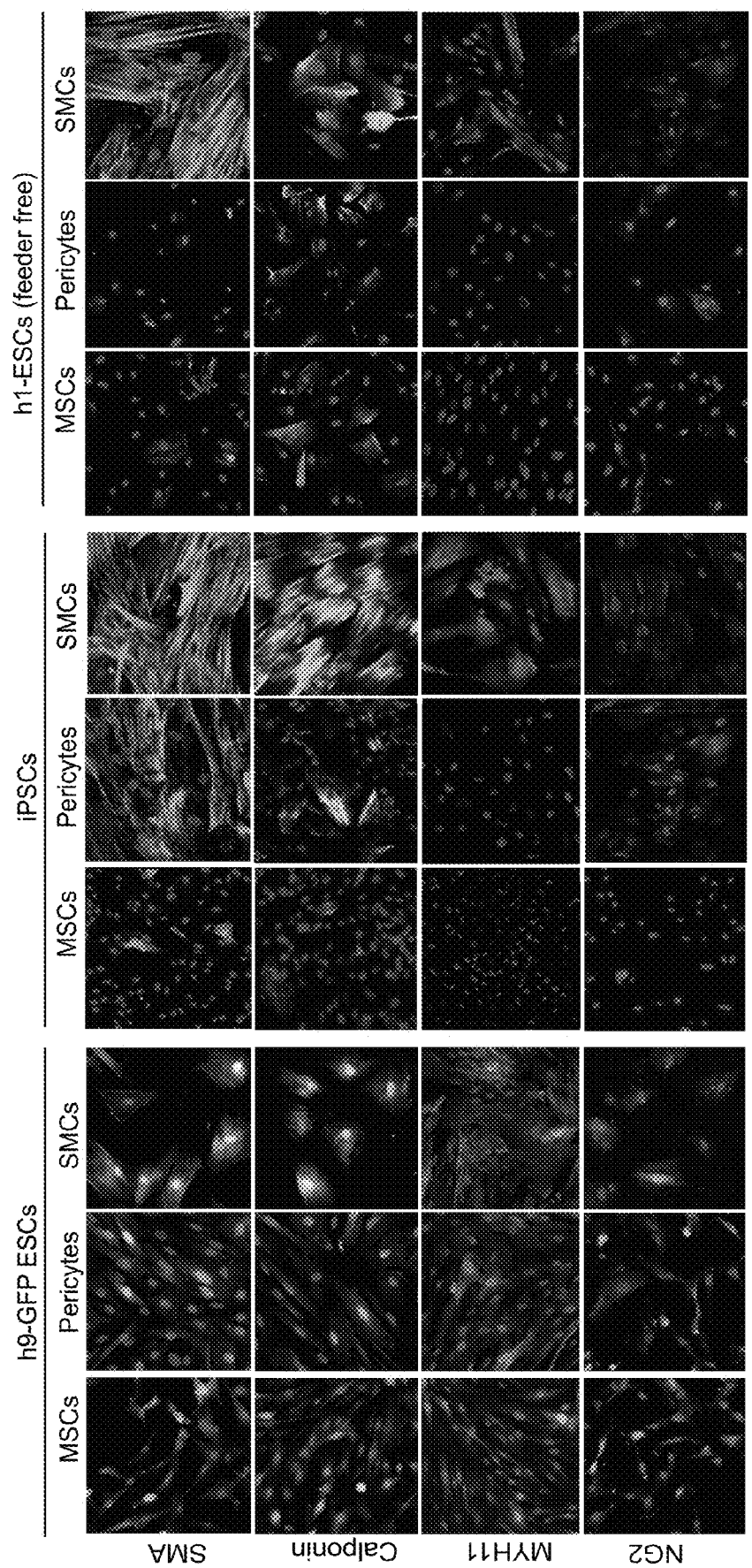
FIG. 8 presents images of pericytes and SMCs derived from H9-EGFP and iPSCs and H1-ESCs. Cells were differentiated under chemically defined conditions. Immunohistochemistry was performed using antibodies specific to SMA, Calponin, Myh11, and NG2 to characterize vasculogenic cells.

Because embryonic mesenchyme originating from lateral plate/splanchnic mesoderm contributes to the formation of pericytes and SMCs (reviewed in Armulik et al., Developmental Cell 21:193-215 (2011); Majesky, Arterioscler Thromb Vasc Biol 27:1248-58 (2007)), it was hypothesized that MAB-derived mesenchymal colonies have a potential to differentiate into vasculogenic cells in addition to skeletogenic MSCs. Mouse embryonic studies demonstrated the PDGF-B/PDGFRβ signaling plays the most critical role in pericyte development. See Leeven et al., Genes & Development 8:1875-87 (1994); Soriano, Genes & Development 8:1888-96 (1994). Therefore, to induce pericyte formation, we transferred mesenchymal colonies to collagen- and fibronectin-coated plastic and cultured them with PDGF-BB (FIG. 1B). Pericytes generated in these conditions were proliferative (FIGS. 7B-C) and showed moderate expression of RGS5, NG2, CD13, PDGFRβ, and α-SMA, thus indicating that the cells exhibited features of immature pericytes (FIGS. 2A, 2B, and 3A). Using this approach, we were able to induce similar cells from various hESCs and iPSCs, including H1, H9 hESCs, and DF-19-9-7T fibroblast-derived iPSCs (FIG. 8). The iPCs can be maintained up to 12 passages, maintaining a highly pure phenotype and remaining largely in an immature state with gradual senescence observed during passages 8 to 12.

Figures 9A, 9B, 9C:
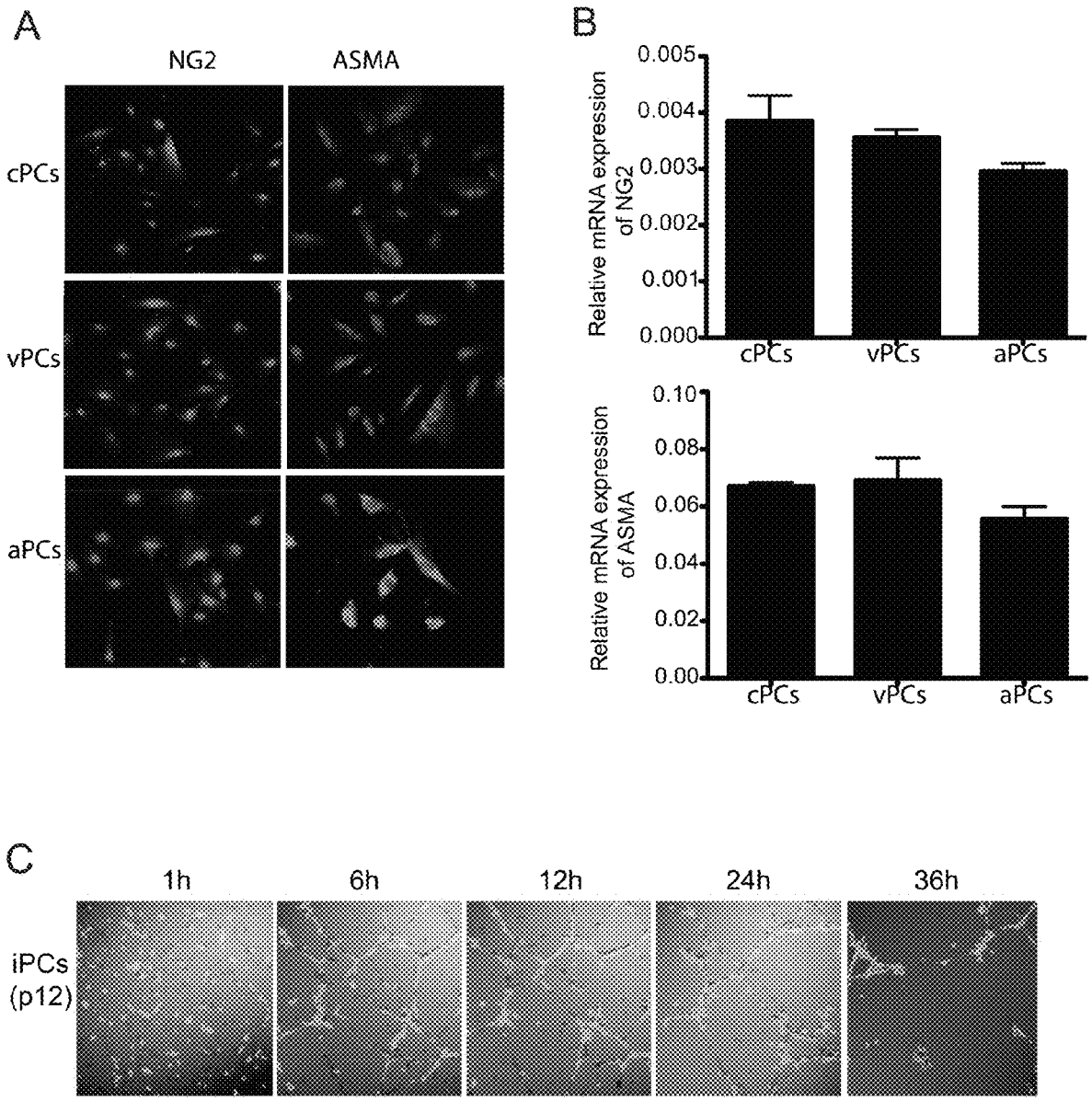
FIGS. 9A-9C present data characterizing immature pericytes and mature pericytes following extended passaging. (A) Immunohistochemistry and (B) mRNA expression data obtained for mature capillary, venule, and arteriole pericytes expanded in pericytes medium for 5 passages. (C) Stabilization of vascular tubes by immature pericytes with extended passaging. The cells were incubated for different time points and photographed using Nikon Eclipse Ti-E, configured with an MR confocal system and motorized stage (Nikon Instruments Inc., Melville, NY).

In the human body, pericytes are phenotypically and functionally heterogenous, with the cells of small arterial, venous, and capillary vessels as well as tissue specific vascular beds showing distinct features. In situ phenotypic analysis demonstrated that pericytes lining the capillaries can be distinguished based on expression NG2 and smooth muscle actin (SMA). NG2$^{high}$SMA$^-$ phenotype is characteristic of the capillaries pericytes, NG2$^{low}$SMA$^+$ venules pericytes and NG2$^{high}$SMA$^{high}$ of the arterioles pericytes. See Crisan et al., Annals of the New York Academy of Sciences 1176:118-123 (2009); Crisan et al., Cell Stem Cells 3:301-313 (2008). Because recruitment of pericytes to the vessels and their maturation status are both regulated by PDGF, TGFβ, EGF, and VEGF signaling, we explored whether modulators of these pathways can affect maturation and specification of iPSC-derived immature PCs. We have found that exposure of iPCs with SB431542 (10 μM) and PDGF (50 ng/ml) induced NG2$^{high}$SMA$^-$ capillary pericytes. NG2$^{low}$SMA$^+$ venules pericytes were induced in cultures with SB431542 (10 μM), PDGF (25 ng/ml), and VEGF (25 ng/ml). NG2$^{high}$SMA$^{high}$ arterioles pericytes were induced with SB431542 (10 μM), PDGF (10 ng/ml), VEGF (10 ng/ml), and EGF (5 ng/ml) (FIG. 2D). When expanded in pericyte medium, we found that three distinct phenotypes of the three types of mature pericytes can be maintained for 2-3 passages only. However, after passage 5, we did not see any significant differences between markers on pericytes induced in three different conditions, although they still maintain the mature pericyte phenotype signified by high NG2 and SMA expression (FIGS. 9A-B).

Induction of smooth muscle cells from MABs: Although molecular profiling data revealed that ACTA2 expression is activated very early during hPSC differentiation on OP9, and could be detected at a high level in MAB colonies (FIG. 3B), the significant expression of other smooth muscle genes such as MYOCD, MYH11, and CNN1 was not detected at this stage, thereby indicating that cells forming MAB colonies do not have features of mature smooth muscles. To find out whether smooth muscle cells can be induced from MAB colonies, we transferred these colonies into cultures supplemented with known inducers of smooth muscle differentiation, namely TGFβ and sphingosylphosphorylcholine (SPC) (FIG. 1). See Cheung et al., Nature Biotechnology 30:165-173 (2012); Chambers et al., Am J Pathol 162:533-546 (2003)). As shown in FIGS. 2A-C and FIGS. 3A-B, cells cultured in these conditions acquired expression of typical smooth muscle molecules markers as determined by immunofluorescent staining, FACS, PCR, and molecular profiling, strongly indicating that TGFβ and SPC treatment induces SMCs from mesenchymal precursors. The SMC potential was consistent among different hPSC line and we were able to obtain smooth muscles from H9 hESCs and DF-19-9-7T fibroblast-derived iPSCs as well (FIG. 8).

In contrast to MSCs and iPCs, SMCs derived from MAB colonies lost proliferative potential and could not be expanded significantly in culture. However, we found that MSCs generated from MABs retain SMC potential even after passage 4 (FIGS. 7B-D). Interestingly, in contrast to SMCs, the capacity to generate pericytes was limited to MAB colonies and we were not able to induce pericytes with PDGFβ with MSC lines even at early passages.

Functional characterization of vasculogenic cells: To study the functional properties of MAB-derived vasculogenic cells we evaluated the potential of these cells to stabilize vascular tubes using an in vitro assay. As shown in FIG. 4A, tubes formed by HUVEC in Matrigel were unstable and dissolved within 48 hours. However, the addition of both MSCs and iPCs, but not SMCs, to cultures stabilized the tubes. The iPCs demonstrated more effect on the tube stability as compared to MSCs. The effect on tube stabilizing properties was observed in early passage cells, but was diminished in iPCs expanded for more than 9-10 passages (FIG. 9C). The mature pericytes (capillary, venules, and arterioles) stabilized tubes for more than 6 days (FIG. 4B). The length of tube and retention capacity was evaluated for MSCs, iPCs, and SMCs and it showed that tube length was well maintained by iPCs and retention capacity was very high compared to MSCs and SMCs (FIGS. 4C-D).

Figures 5A, 5B, 5C, 5D:
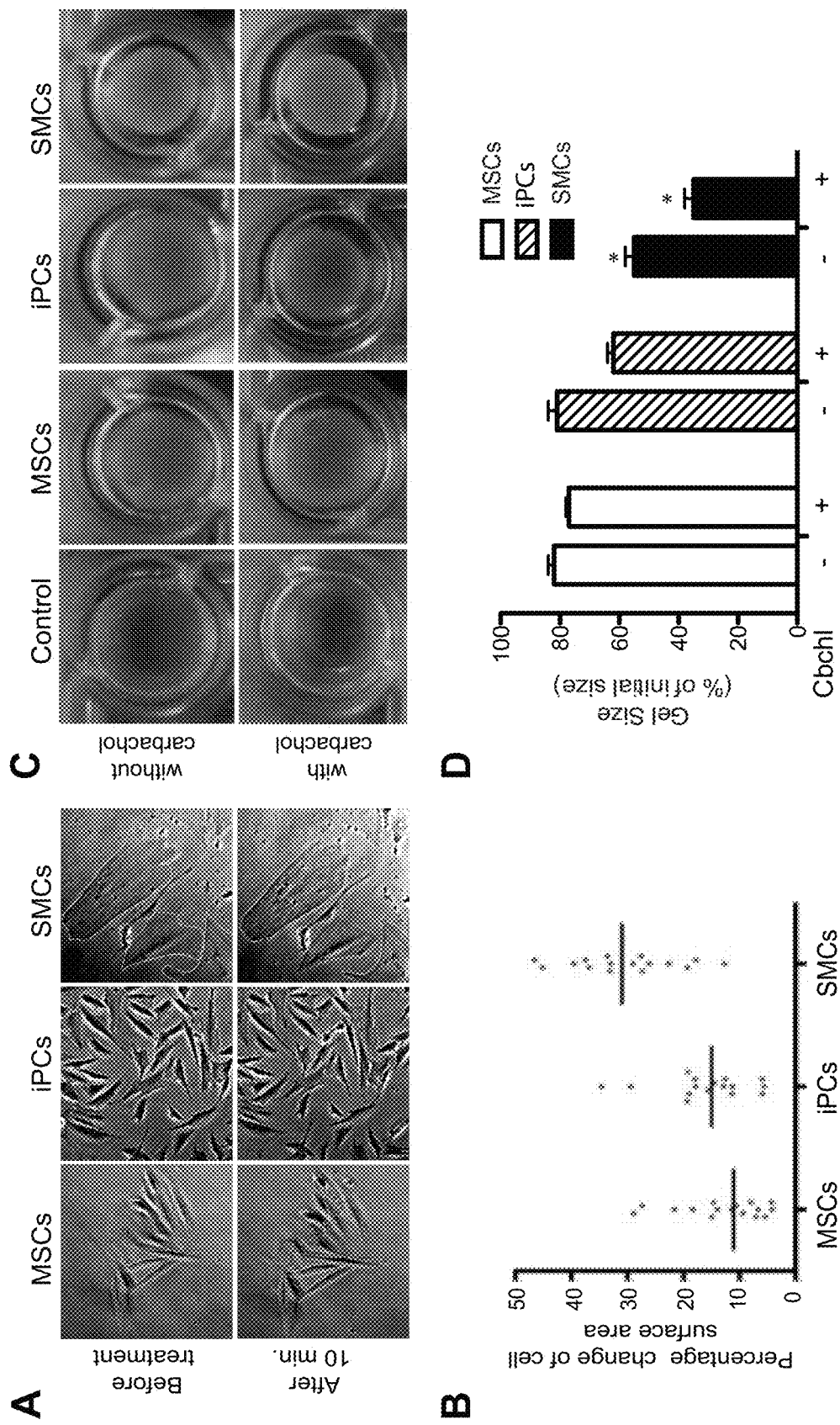
FIGS. 5A-5D provide images and data evaluating the contractile properties of H1-hESC-derived MSCs, iPCs, and SMCs. (A) Phase contrast images of cells treated with carbachol (100 μM). (B) Surface area of each cell was determined using ImageJ software (NIMH, Bethesda, MD) and % change in surface area was calculated. Error bars represent mean±SE of three independent experiments (*p<0.01). (C) MSCs, Pericytes or SMCs were embedded in collagen gel lattices with or without carbachol, and gel contraction was digitally photographed at 48 hours. (D) The size (area) of the gel lattices was determined with ImageJ software (NIMH, Bethesda, MD), and the relative lattice area was obtained by dividing the area at a particular time point by the initial area of the lattice and graphed. Results are displayed as mean±SE of three independent experiments ($*p<0.01$).

To determine the contractile properties of generated cells, we performed time-lapse studies of cells treated with carbachol (100 μM) for 10 minutes. Following treatment, SMCs contracted in tonic fashion and showed a 25-35% change in the surface area (FIGS. 5A-B). The contractile property of SMCs was confirmed using a collagen gel assay, which demonstrated a change 30-40% of the initial gel size (FIGS. 5C-D). The ability to contract was a distinct property of SMCs. In contrast to SMCs, iPCs and MSCs showed very little or complete lack of, contractile potential.

Figure 6:
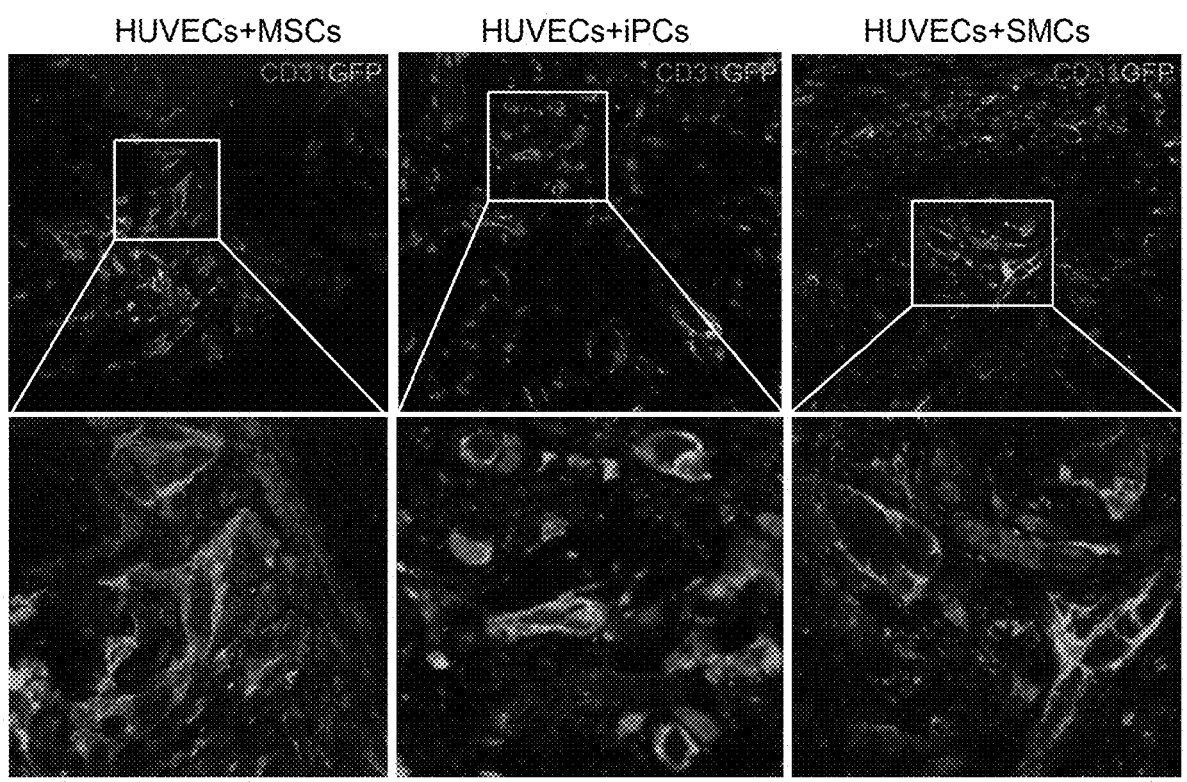
FIG. 6 is a series of images collected for functional characterization of hPSC-derived pericytes and SMC in vivo. Matrigel plugs were harvested two weeks after the subcutaneous implantation of hPSC-derived iPCs, SMCs, or MSCs with HUVECs (1:2). Histological sections were double immune-stained with human antibodies specific to PECAM1 (Platelet endothelial cell adhesion molecule-1; also known as CD31) and to GFP.

To further evaluate the functional properties of MAB-derived vasculogenic cells, HUVECs were embedded with iPCs, MSCs, or SMCs (2:1) in a Matrigel-fibrin matrix containing the growth factors VEGF and FGF-2. HUVECs were mixed with h9ESC-GFP derived MSCs, pericytes, or SMCs (2:1) in 500 μl Matrigel (growth factor reduced; BD Biosciences) and fibrinogen (final concentration 2 mg/ml; Calbiochem) containing different growth factors (250 ng/ml each of VEGF and bFGF). Thrombin (0.4 U; Calbiochem) was added to the mixture. Portions of the embedded cell matrix was subcutaneously implanted into NOD-SCID mice. Matrix was injected subcutaneously on each side lateral to the abdominal midline region into 8-10 weeks old NOD-SCID mice. Implants were retrieved from mice euthanized 14 days post-injection. The implants were fixed overnight in 10% neutral buffered formalin, embedded in paraffin, and sectioned for immunohistochemistry. Implants were analyzed for the formation of a human EC-derived neovasculature. Antibodies specific to human CD31 (also known as PECAM-1) were used to visualize transplanted endothelial cells, and antibodies specific to GFP were used to detect recruited iPCs, SMCs, and MSCs. The resulting implant vasculature consisted almost exclusively of human ECs. Most of the growing neovessels had recruited pericytes as compared to MSCs and SMCs (FIG. 6).

In sum, these studies revealed a hierarchy of mesodermal vasculogenic progenitors, which can be applied to explore the molecular pathways leading to specification and diversification of vasculogenic lineages in humans. In addition, these studies established MABs as multipotent skeletogenic and vasculogenic progenitors with a potential to provide all essential components of the soft tissues and vasculature for therapeutic tissue engineering.

We claim:

1. A method for generating an isolated population of primate vasculogenic cells, the method comprising:
   (a) culturing a colony of primate mesenchymoangioblasts (MAB)-derived cells comprising PDGFRB+ (Platelet Derived Growth Factor Receptor B+)/EMCN$^{high}$/CD105$^{low}$; CD248$^-$/CD73$^-$/CD31$^-$ mesenchymal progenitors on a culture plate having a coating comprising fibronectin, gelatin or collagen, in a serum-free culture medium comprising about 5 ng/mL to about 15 ng/mL of Platelet-Derived Growth Factor-BB (PDGF-BB) and about 20 ng/mL of fibroblast growth factor 2 (FGF2) that promotes differentiation of the MAB-derived mesenchymal progenitors to immature pericytes having a RGS5$^+$ (Regulator of G-protein Signaling 5$^+$)/PDGFRβ$^+$/ANG-1$^+$ (angiopoietin-1$^+$)/CD146$^+$/CD44$^+$/CD13$^+$/NGY (Nerve/Glial antigen 2$^+$)/CD73$^+$ expression profile;
   (b) culturing the immature pericytes on the coated culture plate in the presence of maturation culture medium comprising TGFβ receptor inhibitor and PDGF-BB under conditions that promote maturation of the immature pericytes into a mature pericyte population that is capillary pericytes, venule pericytes, or arteriole pericytes; and
   (c) isolating the mature pericyte cells.

2. The method of claim 1, wherein the primate is human.

3. The method of claim 1, wherein the TGFβ receptor inhibitor is SB-431542.

4. The method of claim 1, wherein the mature pericyte is a NG2$^{high}$/α-SMA10$^{high}$/RGS5$^+$ capillary pericyte.

5. The method of claim 1, wherein the maturation culture medium further comprises 10 μM SB-431542, 25 ng/mL PDGF-BB, and 25 ng/mL of Vascular Endothelial Growth Factor-A (VEGF), and wherein the mature pericyte is a NG2$^{low}$/α-SMA$^{high}$/RGS5$^+$ venule pericyte.

6. The method of claim 1, wherein the maturation culture medium further comprises 10 μM SB-431542, 10 ng/mL PDGF-BB, 10 ng/mL VEGF, and 5 ng/mL Epidermal Growth Factor 2 (EGF2), and wherein the mature pericyte is a NG2$^{high}$/α-SMA$^{high}$/RGS5$^+$ arteriole pericyte.

7. The method of claim 1, wherein the colony of mesenchymal progenitors is clonal.

8. The method of claim 1, wherein the colony of mesenchymal progenitors is polyclonal.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: ASMA oligonucleotide primer

<400> SEQUENCE: 1
gtgttgcccc tgaagagcat                                               20

<210> SEQ ID NO 2
<211> LENGTH: 21
<212> TYPE: DNA
<213> ORGANISM: Artificial Sequence
<220> FEATURE:
<223> OTHER INFORMATION: ASMA oligonucleotide primer

<400> SEQUENCE: 2
gctgggacat tgaaagtctc a                                             21

<210> SEQ ID NO 3
<211> LENGTH: 20
<212> TYPE: DNA
<213> ORGANISM: Artificial Sequence
<220> FEATURE:
<223> OTHER INFORMATION: NG2 oligonucleotide primer

<400> SEQUENCE: 3
gtcttttgag gctgcctgtc                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: NG2 oligonucleotide primer

<400> SEQUENCE: 4
ctgtgtgacc tggaagagca                                          20

<210> SEQ ID NO 5
<211> LENGTH: 21
<212> TYPE: DNA
<213> ORGANISM: Artificial Sequence
<220> FEATURE:
<223> OTHER INFORMATION: PDGFR-beta oligonucleotide primer

<400> SEQUENCE: 5
tgcagcacca ctccgacaag c                                        21

<210> SEQ ID NO 6
<211> LENGTH: 21
<212> TYPE: DNA
<213> ORGANISM: Artificial Sequence
<220> FEATURE:
<223> OTHER INFORMATION: PDGFR-beta oligonucleotide primer

<400> SEQUENCE: 6
tcgctctccc cggtcaagga c                                        21

<210> SEQ ID NO 7
<211> LENGTH: 21
<212> TYPE: DNA
<213> ORGANISM: Artificial Sequence
<220> FEATURE:
<223> OTHER INFORMATION: Caldesmon oligonucleotide primer

<400> SEQUENCE: 7
ctggcttgaa ggtaggggtt t                                        21

<210> SEQ ID NO 8
<211> LENGTH: 21
<212> TYPE: DNA
<213> ORGANISM: Artificial Sequence
<220> FEATURE:
<223> OTHER INFORMATION: Caldesmon oligonucleotide primer

<400> SEQUENCE: 8
ttgggagcag gtgacttgtt t                                        21

<210> SEQ ID NO 9
<211> LENGTH: 21
<212> TYPE: DNA
<213> ORGANISM: Artificial Sequence
<220> FEATURE:
<223> OTHER INFORMATION: RGS5 oligonucleotide primer

<400> SEQUENCE: 9
tccagggaat cacgccactg c                                        21

<210> SEQ ID NO 10
<211> LENGTH: 22
<212> TYPE: DNA
<213> ORGANISM: Artificial Sequence
<220> FEATURE:
<223> OTHER INFORMATION: RGS5 oligonucleotide primer

<400> SEQUENCE: 10
agccagactc agttggtgac ct                                       22
```

```
<210> SEQ ID NO 11
<211> LENGTH: 20
<212> TYPE: DNA
<213> ORGANISM: Artificial Sequence
<220> FEATURE:
<223> OTHER INFORMATION: MYOCD oligonucleotide primer

<400> SEQUENCE: 11
aagcgccatc tcttgaggta                                              20

<210> SEQ ID NO 12
<211> LENGTH: 17
<212> TYPE: DNA
<213> ORGANISM: Artificial Sequence
<220> FEATURE:
<223> OTHER INFORMATION: MYOCD oligonucleotide primer

<400> SEQUENCE: 12
gcgcctttat tttgacc                                                 17

<210> SEQ ID NO 13
<211> LENGTH: 20
<212> TYPE: DNA
<213> ORGANISM: Artificial Sequence
<220> FEATURE:
<223> OTHER INFORMATION: MYH11 oligonucleotide primer

<400> SEQUENCE: 13
ggaggatgag atcctggtca                                              20

<210> SEQ ID NO 14
<211> LENGTH: 20
<212> TYPE: DNA
<213> ORGANISM: Artificial Sequence
<220> FEATURE:
<223> OTHER INFORMATION: MYH11 oligonucleotide primer

<400> SEQUENCE: 14
ttagccgcac ttccagttct                                              20

<210> SEQ ID NO 15
<211> LENGTH: 22
<212> TYPE: DNA
<213> ORGANISM: Artificial Sequence
<220> FEATURE:
<223> OTHER INFORMATION: Calponin oligonucleotide primer

<400> SEQUENCE: 15
caaccaccac gcacacaact ac                                           22

<210> SEQ ID NO 16
<211> LENGTH: 20
<212> TYPE: DNA
<213> ORGANISM: Artificial Sequence
<220> FEATURE:
<223> OTHER INFORMATION: Calponin oligonucleotide primer

<400> SEQUENCE: 16
ggtccagcca agagcagcag                                              20

<210> SEQ ID NO 17
<211> LENGTH: 21
<212> TYPE: DNA
<213> ORGANISM: Artificial Sequence
<220> FEATURE:
<223> OTHER INFORMATION: VE-cadherin oligonucleotide primer
```

```
<400> SEQUENCE: 17
gatcaagtca agcgtgagtc g                                          21

<210> SEQ ID NO 18
<211> LENGTH: 20
<212> TYPE: DNA
<213> ORGANISM: Artificial Sequence
<220> FEATURE:
<223> OTHER INFORMATION: VE-cadherin oligonucleotide primer

<400> SEQUENCE: 18
agcctctcaa tggcgaacac                                            20
```